US011464465B2

(12) United States Patent
Kobayashi et al.

(10) Patent No.: US 11,464,465 B2
(45) Date of Patent: Oct. 11, 2022

(54) X-RAY DIAGNOSIS APPARATUS AND CONSOLE

(71) Applicant: CANON MEDICAL SYSTEMS CORPORATION, Otawara (JP)

(72) Inventors: Yoshiteru Kobayashi, Sakura (JP); Keisuke Sugawara, Otawara (JP); Yosuke Kayukawa, Otawara (JP); Hiroshi Komatsu, Yokohama (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 143 days.

(21) Appl. No.: 16/787,192

(22) Filed: Feb. 11, 2020

(65) Prior Publication Data

US 2020/0253569 A1 Aug. 13, 2020

(30) Foreign Application Priority Data

Feb. 13, 2019 (JP) .............................. JP2019-023879

(51) Int. Cl.
*A61B 6/06* (2006.01)
*G21K 1/02* (2006.01)
(Continued)

(52) U.S. Cl.
CPC ................... *A61B 6/06* (2013.01); *A61B 6/40* (2013.01); *A61B 6/405* (2013.01); *A61B 6/46* (2013.01);
(Continued)

(58) Field of Classification Search
CPC ........ A61N 5/10; A61N 5/103; A61N 5/1036; A61B 6/06; A61B 6/40; A61B 6/4035; A61B 6/405; A61B 6/46; A61B 6/461; A61B 6/462; A61B 6/465; A61B 6/467; A61B 6/54; G01N 2223/30; G01N 2223/306; G01N 2223/313;
(Continued)

(56) References Cited

U.S. PATENT DOCUMENTS

2009/0238331 A1* 9/2009 Kargar ..................... A61B 6/06
378/19
2013/0156154 A1 6/2013 Watanabe et al.
(Continued)

FOREIGN PATENT DOCUMENTS

JP 7-129890 A 5/1995
JP 2009-82205 A 4/2009
(Continued)

*Primary Examiner* — Anastasia Midkiff
(74) *Attorney, Agent, or Firm* — Oblon, McClelland, Maier & Neustadt, L.L.P.

(57) ABSTRACT

An X-ray diagnosis apparatus includes an X-ray limiter having four diaphragm blades and a console on which four physical operating units that correspond to the four diaphragm blades are placed at four positions. When viewed from the side of the operator of the console, the four operating units are placed on the far side, the near side, the left side, and the right side. The far-side operating unit, the near-side operating unit, the left-side operating unit, and the right-side operating unit correspond to the upper diaphragm blade, the lower diaphragm blade, the left-side diaphragm blade, and the right-side diaphragm blade, respectively, with reference to an X-ray image displayed in a display.

20 Claims, 11 Drawing Sheets

(51) Int. Cl.
   *G21K 1/04*     (2006.01)
   *A61B 6/00*     (2006.01)
   *A61B 6/04*     (2006.01)

(52) U.S. Cl.
   CPC .............. *A61B 6/467* (2013.01); *G21K 1/025*
   (2013.01); *G21K 1/04* (2013.01); *G21K 1/046*
   (2013.01); *A61B 6/0407* (2013.01); *A61B 6/4435* (2013.01); *A61B 6/485* (2013.01); *A61B 6/54* (2013.01)

(58) Field of Classification Search
   CPC ....... G01N 2223/314; G01N 2223/316; G01N 2223/32; G01N 2223/321; G21K 1/02; G21K 1/025; G21K 1/04; G21K 1/046; G21K 5/04; H01J 37/06; H01J 2237/045; H01J 2237/0455; H01J 2237/0456; H01J 2237/0458
   See application file for complete search history.

(56) References Cited

U.S. PATENT DOCUMENTS

| | | | |
|---|---|---|---|
| 2013/0315370 A1* | 11/2013 | Watanabe | A61B 6/487 378/42 |
| 2016/0058399 A1 | 3/2016 | Narabu et al. | |
| 2016/0320322 A1* | 11/2016 | Suzuki | G21K 1/04 |
| 2017/0245826 A1 | 8/2017 | Kasaoka | |
| 2018/0368788 A1 | 12/2018 | Kobayashi et al. | |
| 2019/0110827 A1* | 4/2019 | Liu | A61B 6/487 |

FOREIGN PATENT DOCUMENTS

| | | |
|---|---|---|
| JP | 2013-128585 A | 7/2013 |
| JP | 2017-153591 A | 9/2017 |
| JP | 2019-5346 A | 1/2019 |
| WO | WO 2014/181870 A1 | 11/2014 |

* cited by examiner

X-RAY DIAGNOSIS APPARATUS AND CONSOLE

CROSS-REFERENCE TO RELATED APPLICATIONS

This application is based upon and claims the benefit of priority from Japanese Patent Application No. 2019-023879, filed on Feb. 13, 2019; the entire contents of which are incorporated herein by reference.

FIELD

Embodiments described herein relate generally to an X-ray diagnosis apparatus and a console.

BACKGROUND

An X-ray diagnosis apparatus includes a collimator that performs sharp focusing of the X-rays generated from an X-ray tube and irradiates a subject with the X-rays; and a compensating filter that is inserted in some part of the X-ray irradiation field and that causes X-ray attenuation in that part. The collimator is a movable diaphragm and is configured using, for example, four slidable diaphragm blades.

The operator of an X-ray diagnosis apparatus adjusts the X-ray irradiation field, which is formed by the diaphragm blades, in order to prevent the subject from unnecessary radiation exposure; and inserts compensating filters in some part of the X-ray irradiation field with the aim of halation suppression. More particularly, the operator adjusts the X-ray irradiation field by sliding the diaphragm blades via a console and adjusting the arrangement of the four diaphragm blades; and adjusts the area for insertion of the compensating filters by moving or rotating the compensating filters via the console and adjusting the positioning of the compensating filters. However, it is not possible for the operator to intuitively understand the manner in which the console needs to be operated for adjusting the diaphragm blades and the compensating filters in the desired arrangement, and that may sometimes hinder the procedure.

DETAILED DESCRIPTION

An X-ray diagnosis apparatus comprises an X-ray limiter and a console. The X-ray limiter includes four diaphragm blades. Four physical operating units that correspond to the four diaphragm blades are placed at four positions on the console. When viewed from side of operator of the console, the four operating units are placed on far side, near side, left side, and right side. Far-side operating unit, near-side operating unit, left-side operating unit, and right-side operating unit correspond to upper diaphragm blade, lower diaphragm blade, left-side diaphragm blade, and right-side diaphragm blade, respectively, with reference to an X-ray image displayed in a display. An operation of moving the far-side operating unit in far-side direction results in movement of the upper diaphragm blade in upward direction of the X-ray image displayed in the display, and an operation of moving the far-side operating unit in near-side direction results in movement of the upper diaphragm blade in downward direction of the X-ray image displayed in the display. An operation of moving the near-side operating unit in far-side direction results in movement of the lower diaphragm blade in upward direction of the X-ray image displayed in the display, and an operation of moving the near-side operating unit in near-side direction results in movement of the lower diaphragm blade in downward direction of the X-ray image displayed in the display. An operation of moving the left-side operating unit in leftward direction results in movement of the left-side diaphragm blade in leftward direction of the X-ray image displayed in the display, and an operation of moving the left-side operating unit in rightward direction results in movement of the left-side diaphragm blade in rightward direction of the X-ray image displayed in the display. An operation of moving the right-side operating unit in leftward direction results in movement of the right-side diaphragm blade in leftward direction of the X-ray image displayed in the display, and an operation of moving the right-side operating unit in rightward direction results in movement of the right-side diaphragm blade in rightward direction of the X-ray image displayed in the display.

Exemplary embodiments of the X-ray diagnosis apparatus and the console are described below in detail with reference to the accompanying drawings.

Figure 1:
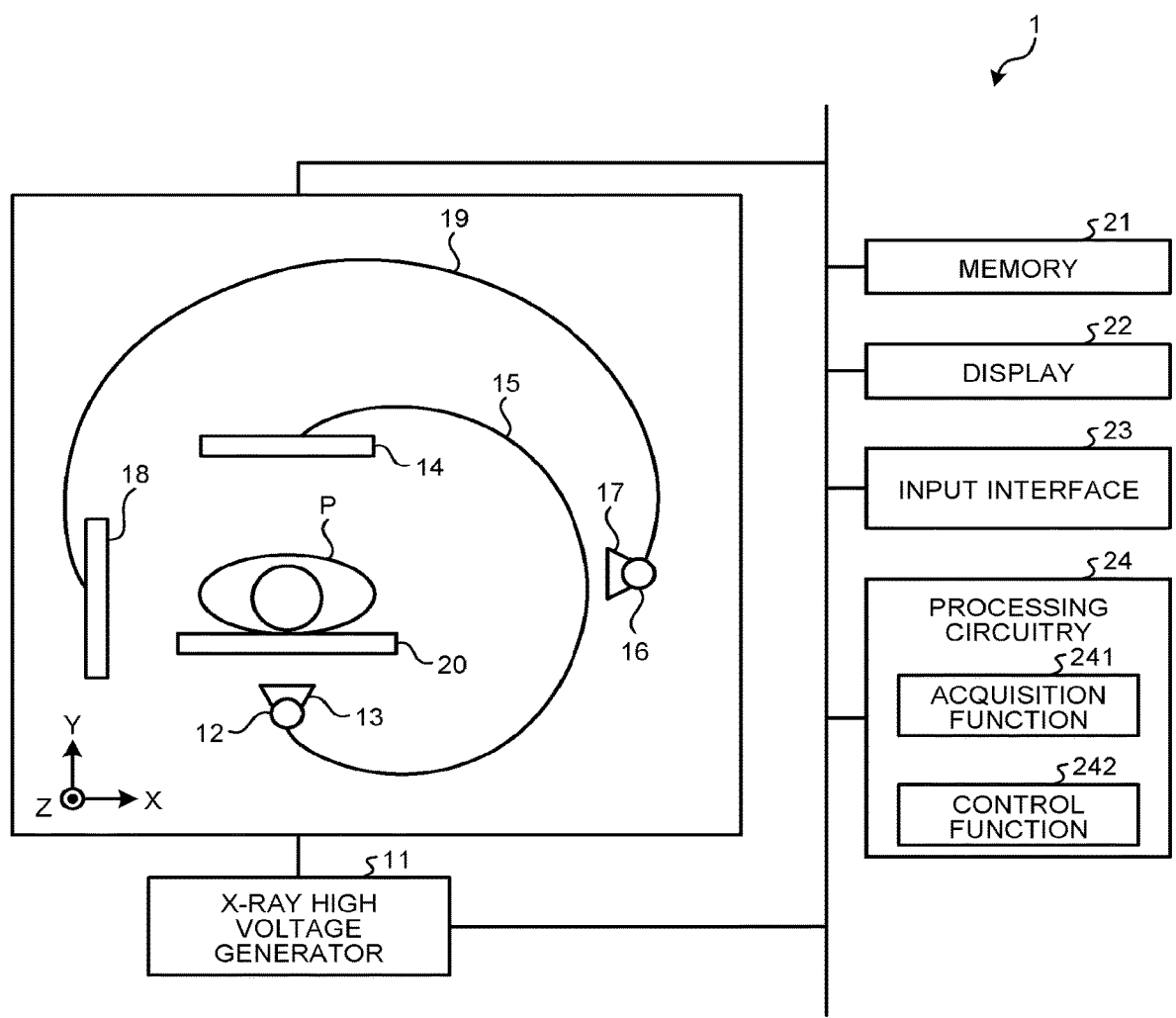
FIG. 1 is a block diagram illustrating an exemplary configuration of an X-ray diagnosis apparatus according to a first embodiment.

Firstly, the explanation is given about a first embodiment. In the first embodiment, the explanation is given with reference to an X-ray diagnosis apparatus 1 illustrated in FIG. 1. FIG. 1 is a block diagram illustrating an exemplary configuration of the X-ray diagnosis apparatus 1 according to the first embodiment.

As illustrated in FIG. 1, the X-ray diagnosis apparatus 1 includes an X-ray high-voltage generator 11, a first X-ray tube 12, a first X-ray limiter 13, a first X-ray detector 14, a first arm 15, a second X-ray tube 16, a second X-ray limiter 17, a second X-ray detector 18, a second arm 19, a tabletop 20, a memory 21, a display 22, an input interface 23, and processing circuitry 24. That is, the X-ray diagnosis apparatus is a biplane device including the first arm 15 and the second arm 19. Moreover, the input interface 23 includes a console (described later).

The X-ray high-voltage generator 11 supplies a high voltage to the first X-ray tube 12 and the second X-ray tube 16 under the control of the processing circuitry 24. For example, the X-ray high-voltage generator 11 includes electrical circuitry such as a transformer and a rectifier; includes a high-voltage generation device that generates a high voltage to be applied to the first X-ray tube 12 and the second X-ray tube 16; and includes an X-ray control device that controls the output voltage according to the X-rays bombarded from the first X-ray tube 12 and the second X-ray tube 16. The high-voltage generation device can be of the transformer type or of the inverter type.

The first X-ray tube 12 as well as the second X-ray tube 16 is a vacuum tube including a cathode (a filament) that generates thermions and an anode (a target) that generates X-rays in response to the collision of thermions. The first X-ray tube 12 as well as the second X-ray tube 16 generates X-rays by bombarding thermions from the cathode toward the anode using the high voltage supplied from the X-ray high-voltage generator 11.

The first X-ray limiter 13 as well as the second X-ray limiter 17 includes a collimator that narrows down the X-ray irradiation range and a filter that regulates the X-rays.

The collimator in the first X-ray limiter 13 includes, for example, four slidable diaphragm blades that, when slid, results in sharp focusing of the X-rays generated by the first X-ray tube 12 and irradiation of a subject P with the X-rays. The diaphragm blades are plate-like members made of lead, and are disposed near the X-ray irradiation hole of the first X-ray tube 12 for enabling adjustment of the X-ray irradiation range. In an identical manner, in the collimator of the second X-ray limiter 17, when the diaphragm blades are slid, it results in sharp focusing of the X-rays generated by the second X-ray tube 16 and irradiation of the subject P with the X-rays.

The filters provided in the first X-ray limiter 13 and the second X-ray limiter 17 adjust the radiation dose and the radiation quality of the transmissive X-rays with the aim of reducing the exposure dose of the subject P and enhancing the image quality of the X-ray image data. For example, the first X-ray limiter 13 and the second X-ray limiter 17 include various X-ray filters such as a radiation quality adjustment filter, compensating filters, and a radiation dose reduction filter. The radiation quality adjustment filter enables varying the radiation quality of the transmissive X-rays depending on the material and the thickness of the filter, and enables achieving reduction in the soft ray components that are easily absorbable by the subject P and reduction in the high-energy components that cause deterioration in the contrast of the X-ray image data. The compensating filters attenuate some of the X-rays, which are irradiated from the X-ray tube, with the aim of suppressing halation. The radiation dose reduction filter attenuates some of the X-rays, which are irradiated from the X-ray tube, in such a way that the X-rays bombarded onto other sites have a lower radiation dose than the X-rays bombarded onto the region of interest, with the aim of reducing the exposure dose of the subject P.

For example, the first X-ray limiter 13 and the second X-ray limiter 17 have a drive mechanism such as a motor and an actuator, and control the X-ray irradiation by operating the drive mechanism according to an input operation received from the operator via the input interface 23. For example, the first X-ray limiter 13 and the second X-ray limiter 17 apply a drive voltage to the drive mechanism according to the input operation, and adjust the arrangement of the diaphragm blades of the collimator and control the irradiation range of the X-rays bombarded onto the subject P. Moreover, for example, the first X-ray limiter 13 and the second X-ray limiter 17 apply a drive voltage to the drive mechanism according to the input operation, and adjust the positions of the compensating filters and the radiation dose reduction filter and control the distribution of the radiation dose of the X-rays. Meanwhile, regarding the operations of the first X-ray limiter 13 and the second X-ray limiter 17 performed via the input interface 23, the explanation is given later.

The tabletop 20 is a board on which the subject P is asked to lie down, and is placed on top of a bed drive device (not illustrated). Thus, the subject P is not a part of the X-ray diagnosis apparatus 1. The bed drive device includes, for example, a drive mechanism such as a motor and an actuator; and operates the drive mechanism under the control of the processing circuitry 24 (described later) and controls the movement/inclination of the tabletop 20. For example, the bed drive device applies a drive voltage to the drive mechanism according to a control signal received from the processing circuitry 24, and moves or inclines the tabletop 20. Meanwhile, when illustrating a device on which the subject P is asked to lie down, a bed is also illustrated. In the bed, for example, the tabletop 20 and the berth drive device are included.

The first X-ray detector 14 and the second X-ray detector 18 are, for example, flat panel detectors (FPDs) in which detection elements are arranged as a matrix. The first X-ray detector 14 detects the X-rays that have transmitted through the subject P after being bombarded from the first X-ray tube 12; and outputs a detection signal corresponding to the detected X-ray dose to the processing circuitry 24. In an identical manner, the second X-ray detector 18 detects the X-rays that have transmitted through the subject P after being bombarded from the second X-ray tube 16; and outputs a detection signal corresponding to the detected X-ray dose to the processing circuitry 24. The first X-ray detector 14 and the second X-ray detector 18 either can be indirect-conversion-type detectors that include a grid, a scintillator array, and an optical sensor array; or can be direction-conversion-type detectors that include a semiconductor device for converting the incident X-rays into electrical signals.

The first arm 15 holds the first X-ray tube 12, the first X-ray limiter 13, and the first X-ray detector 14. More particularly, the first arm 15 holds the first X-ray tube 12 and the first X-ray limiter 13 on the opposite side of the first X-ray detector 14 across the subject P. The first arm 15 is also called a C-arm or a C-type arm. The first arm 15 includes, for example, a drive mechanism such as a motor and an actuator and, under the control of the processing circuitry 24 (described later), operates the drive mechanism for rotates and moving around. For example, as a result of applying a drive voltage to the drive mechanism according to the control signal received from the processing circuitry 24, the first arm 15 rotates/moves the first X-ray tube 12, the first X-ray limiter 13, and the first X-ray detector 14 with respect to the subject P; and controls the X-ray irradiation position and the X-ray irradiation angle.

The second arm 19 holds the second X-ray tube 16, the second X-ray limiter 17, and the second X-ray detector 18. More particularly, the second arm 19 holds the second X-ray tube 16 and the second X-ray limiter 17 on the opposite side of the second X-ray detector 18 across the subject P. The second arm 19 is also called an Ω arm or an Ω-type arm. The second arm 19 includes, for example, a drive mechanism such as a motor and an actuator and, under the control of the processing circuitry 24 (described later), operates the drive mechanism for rotating and moving around. For example, as a result of applying a drive voltage to the drive mechanism according to the control signal received from the processing circuitry 24, the second arm 19 rotates/moves the second X-ray tube 16, the second X-ray limiter 17, and the second X-ray detector 18 with respect to the subject P; and controls the X-ray irradiation position and the X-ray irradiation angle.

The memory 21 is implemented using, for example, a semiconductor memory device such as a random access memory (RAM) or a flash memory; or a hard disk; or an optical disk. For example, the memory 21 is used to store a variety of X-ray image data acquired by the processing circuitry 24. Moreover, the memory 21 is used to store computer programs that correspond to various functions and that are read and executed by the processing circuitry 24. Meanwhile, the memory 21 can alternatively be implemented using a server group (cloud) that is connected to the X-ray diagnosis apparatus 1 via a network.

The display 22 is used to display a variety of information. For example, under the control of the processing circuitry 24, the display 22 displays a graphical user interface (GUI), which is meant for receiving instructions from the operator, and various X-ray images. For example, the display 22 is a liquid crystal display or a cathode ray tube (CRT) display. The display 22 can be a desktop display or can be configured using a tablet terminal that can perform wireless communication with the processing circuitry 24. Meanwhile, the X-ray diagnosis apparatus 1 can include a plurality of displays 22. For example, the X-ray diagnosis apparatus 1 can include two physically-separated displays (dual displays) as the displays 22. Moreover, the displays 22 can be controlled to be mutually associated. For example, the displays 22 can be controlled to display a single continuous area. In that case, the display area in the displays 22 is expanded according to the number of displays 22. Herein, the display 22 represents an example of a display unit meant for displaying X-ray images.

The input interface 23 receives various input operations from the operator, converts the input operations into electrical signals, and outputs the electrical signals to the processing circuitry 24. For example, the input interface 23 is implemented using physical operating units such as a mouse, a keyboard, buttons, sticks for receiving inclination operations, operating units for receiving slide operations, and operating units for receiving rotation operations (for example, trackballs, wheels, knobs, or grips). Moreover, for example, the input interface 23 is implemented using operating units such as a touchpad that enables input operations by touching the operation screen; a touchscreen configured by integrating the display screen and the touchpad; a non-contact input circuit in which an optical sensor is used; or a voice input circuit. Alternatively, the input interface 23 can be configured using a tablet terminal that can perform wireless communication with the processing circuitry 24. Alternatively, for example, the input interface 23 is implemented using electrical signal processing circuitry that receives electrical signals corresponding to input operations from an external input device installed separately from the X-ray diagnosis apparatus 1, and outputs the electrical signals to the processing circuitry 24.

For example, the X-ray diagnosis apparatus 1 includes, as an example of the input interface 23, a console that receives input operations meant for operating the first X-ray limiter 13 and the second X-ray limiter 17. The console is installed on, for example, the bed on which the subject P lies down. The explanation about the console is given later.

The processing circuitry 24 controls the operations of the entire X-ray diagnosis apparatus 1 by executing a acquisition function 241 and a control function 242. For example, the processing circuitry 24 reads a computer program corresponding to the acquisition function 241 from the memory 21, executes it, and acquires the X-ray image data of the subject P.

For example, the acquisition function 241 acquires the X-ray image data of the subject P by controlling a first imaging system including the first X-ray tube 12, the first X-ray limiter 13, the first X-ray detector 14, and the first arm 15. Moreover, for example, the acquisition function 241 acquires the X-ray image data of the subject P by controlling a second imaging system including the second X-ray tube 16, the second X-ray limiter 17, the second X-ray detector 18, and the second arm 19. The acquisition function 241 can be configured to control the operations of the first imaging system and the second imaging system, and to simultaneously acquire the X-ray image data having different imaging directions.

The specific explanation is given about the case in which the images are acquired using the first imaging system. For example, the acquisition function 241 controls the operations of the bed drive device for moving or inclining the tabletop 20. Moreover, the acquisition function 241 controls the operations of the first arm 15 for controlling the imaging position and the imaging angle in the first imaging system. Furthermore, according to an input operation received via the console, the acquisition function 241 controls the operations of the first X-ray limiter 13; adjusts the arrangement of the diaphragm blades of the collimator; and controls the irradiation range of the X-rays bombarded onto the subject P. Moreover, according to an input operation received via a limiting operation console, the acquisition function 241 controls the operations of the first X-ray limiter 13; adjusts the position of the compensating filters; and controls the distribution of the X-ray radiation dose. Furthermore, the acquisition function 241 controls the X-ray high-voltage generator 11; adjusts the voltage to be supplied to the first X-ray tube 12; and controls the radiation dose and the radiation on/off regarding the X-rays bombarded from the first X-ray tube 12 onto the subject P. Moreover, the acquisition function 241 generates the X-ray image data based on the detection signals received from the first X-ray detector 14, and stores the X-ray image data in the memory 21. Meanwhile, the acquisition function 241 can also perform a variety of image processing with respect to the X-ray image data stored in the memory 21. For example, the acquisition function 241 performs noise reduction and scattered-radiation correction using an image processing filter with respect to the X-ray image data.

The processing circuitry 24 also reads a computer program corresponding to the control function 242 from the memory 21, executes the computer program, and performs display control in the display 22. For example, the control function 242 sequentially displays the X-ray images, which are acquired by the acquisition function 241, in the display 22. Herein, the mode in which the acquisition of X-ray images and the display thereof is performed in parallel is referred to as a fluoroscopy mode.

In the X-ray diagnosis apparatus 1 illustrated in FIG. 1, the processing functions are stored in the memory 21 in the form of computer-executable programs. The processing circuitry 24 is a processor that reads the computer programs from the memory 21, executes them, and implements the functions corresponding to the computer programs. In other words, the processing circuitry 24 that has read a computer program gets equipped with the function corresponding to that computer program.

With reference to FIG. 1, the explanation is given about the case in which the processing functions of the acquisition function 241 and the control function 242 are implemented using a single processing circuitry 24. However, the embodiment is not limited by that case. Alternatively, for example, the processing circuitry 24 can be configured by combining a plurality of independent processors, and each processor can be made to execute a computer program to implement a processing function. Still alternatively, the processing functions of the processing circuitry 24 can be appropriately dispersed or integrated among one or more processing circuits.

The term "processor" implies, for example, a central processing unit (CPU), a graphics processing unit (GPU), an application specific integrated circuit (ASIC), or a programmable logic device (for example, a simple programmable logic device (SPLD), a complex programmable logic device (CPLD), or a field programmable gate array (FPGA)). The processor implements functions by reading computer programs from the memory 21 and executing them.

Moreover, with reference to FIG. 1, the explanation is given about the case in which the computer programs corresponding to the processing functions are stored in a single memory 21. However, the embodiment is not limited by that case. Alternatively, for example, a plurality of memories 21 can be arranged in a dispersed manner; and the processing circuitry 24 can read the computer programs from the individual memories 21. Still alternatively, instead of storing the computer programs in the memory 21, they can be directly embedded in the circuit of the processor. In that case, the processor implements the functions by reading the computer programs embedded in the circuit and executing them.

Still alternatively, the processing circuitry 24 can implement the functions using the processor of an external device connected via a network NW. For example, the processing circuitry 24 reads the computer programs corresponding to the functions from the memory 21 and executes them, as well as uses, as computational resources, a server group (cloud) that is connected to the X-ray diagnosis apparatus 1 via the network NW; and implements the functions illustrated in FIG. 1.

Till now, the explanation was given about the X-ray diagnosis apparatus 1. With such a configuration, the X-ray diagnosis apparatus 1 enables achieving enhancement in the operability related to at least either the diaphragm blades or the compensating filters. Given below is the detailed explanation about operating the diaphragm blades in the X-ray diagnosis apparatus 1.

Figure 2:
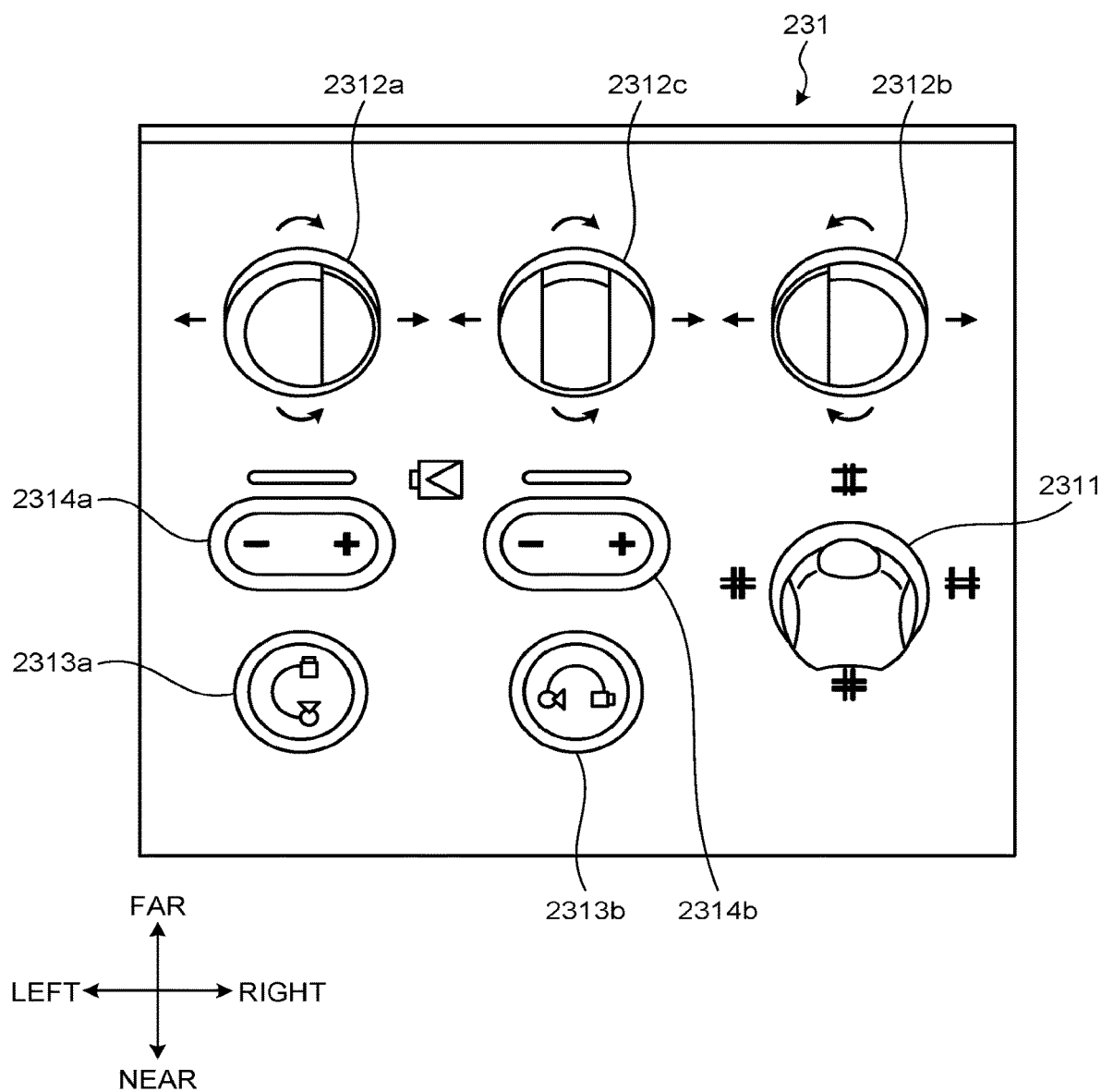
FIG. 2 is a diagram illustrating an example of a console according to the first embodiment.

Firstly, the explanation is given about a diaphragm operation console 231 illustrated in FIG. 2 as an example of the console. FIG. 2 is a diagram illustrating an example of the console according to the first embodiment. As illustrated in FIG. 2, the diaphragm operation console 231 has the following components arranged therein: a diaphragm blade stick 2311; filter sticks 2312a, 2312b, and 2312c; arm switching buttons 2313a and 2313b; and enlargement factor adjustment buttons 2314a and 2314b.

Meanwhile, FIG. 2 is a diagram in which the diaphragm operation console 231 is viewed while facing it. With reference to FIG. 2, the operator operates the diaphragm operation console 231 from the lower side. That is, when viewed from the side of the operator; the far side, the near side, the left side, and the right side can be defined as illustrated in FIG. 2.

The operator performs an input operation with respect to the diaphragm operation console 231 for operating the first X-ray limiter 13 or the second X-ray limiter 17. The acquisition function 241 controls the operations of the first X-ray limiter 13 or the second X-ray limiter 17 according to the input operation received via the diaphragm operation console 231.

The arm switching buttons 2313a and 2313b are switches for changing the operation target. For example, when the arm switching button 2313a is operated, the acquisition function 241 sets the first X-ray limiter 13, which is held by the first arm 15, as the operation target. Then, while the first X-ray limiter 13 is set as the operation target, when an operating unit such as the diaphragm blade stick 2311 or the filter stick 2312a is operated, the acquisition function 241 controls the operations of the first X-ray limiter 13 according to the received input operation. In an identical manner, when the arm switching button 2313b is operated, the acquisition function 241 sets the second X-ray limiter 17, which is held by the second arm 19, as the operation target.

Meanwhile, the arm switching buttons 2313a and 2321b can be configured to detect an operation from the operator as a result of being pressed; or can be configured to detect an operation from the operator based on the variation in the capacitance generated as a result of the touch made by the operator; or can be buttons of some other type. The same is the case about the various buttons explained hereinafter.

The enlargement factor adjustment buttons 2314a and 2314b are buttons for adjusting the enlargement factor of an X-ray image IM displayed in the display 22. For example, when the "+" symbol in the enlargement factor adjustment button 2314a is selected, the processing circuitry 24 increases the enlargement factor of the X-ray image IM displayed in the display 22. Similarly, when the "−" symbol in the enlargement factor adjustment button 2314a is selected, the processing circuitry 24 reduces the enlargement factor of the X-ray image IM displayed in the display 22.

The diaphragm blade stick 2311 is a lever-shaped operating unit that is inclinable in arbitrary directions or predetermined directions, and that receives an inclination operation from the operator. When the diaphragm blade stick 2311 is operated by an operator; the acquisition function 241 moves the diaphragm blades of the first X-ray limiter 13 or the second X-ray limiter 17 according to the direction of inclination of the diaphragm blade stick 2311. The following explanation is given about the case in which the first X-ray limiter 13 is set as the operation target. In that case, the acquisition function 241 moves the diaphragm blades of the first X-ray limiter 13 according to the direction of inclination of the diaphragm blade stick 2311.

Figure 3:
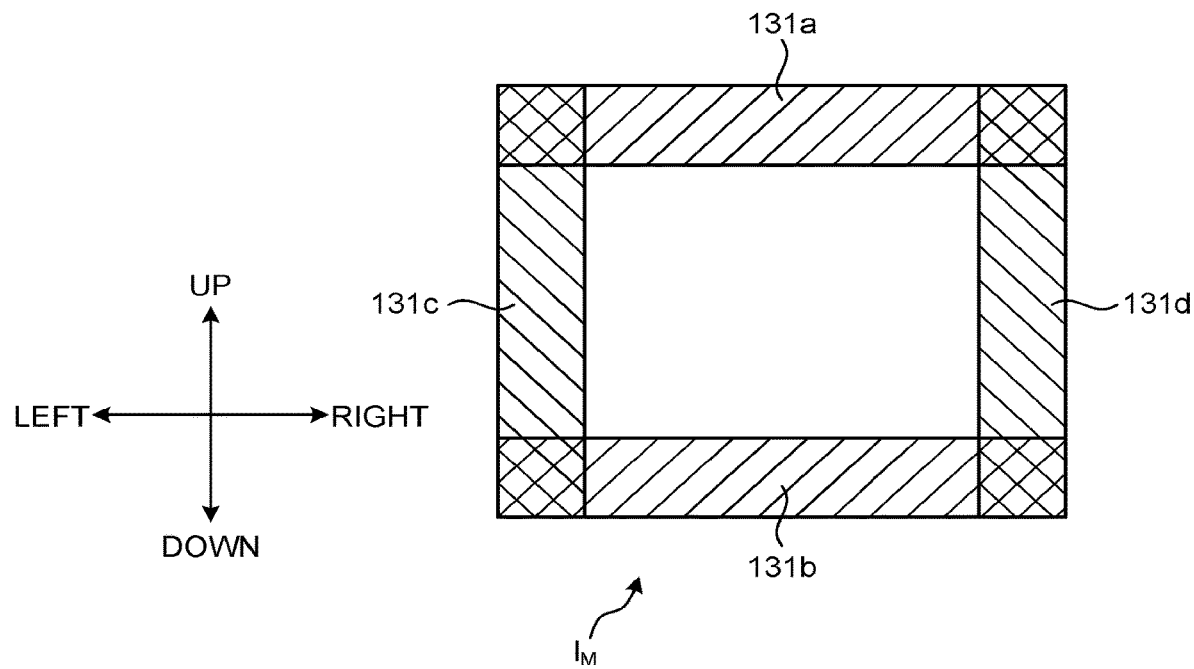
FIG. 3 is a diagram for explaining the arrangement of diaphragm blades according to the first embodiment.

For example, the first X-ray limiter 13 includes a collimator 131 configured using four diaphragm blades 131a, 131b, 131c, and 131d. As illustrated in FIG. 3, the diaphragm blade 131a is a diaphragm blade on the upper side of the X-ray image IM displayed in the display 22. That is, the diaphragm blade 131a blocks the X-rays that are generated in the first X-ray tube 12 and that are bombarded toward the subject area representing the upper side of the X-ray image M displayed in the display 22. FIG. 3 is a diagram for explaining the arrangement of the diaphragm blades according to the first embodiment. When the entire X-ray image IM is displayed in the display 22, the diaphragm blade 131a defines the upper contour of the X-ray irradiation area in the X-ray image IM.

The diaphragm blade 131b is a diaphragm blade on the lower side of the X-ray image IM displayed in the display 22. The diaphragm blade 131c is a diaphragm blade on the left side of the X-ray image IM displayed in the display 22. The diaphragm blade 131d is a diaphragm blade on the right side of the X-ray image IM displayed in the display 22. When the diaphragm blade stick 2311 is operated by the operator; the acquisition function 241 moves the diaphragm blades 131a, 131b, 131c, and 131d according to the direction of inclination of the diaphragm blade stick 2311.

Figure 4:
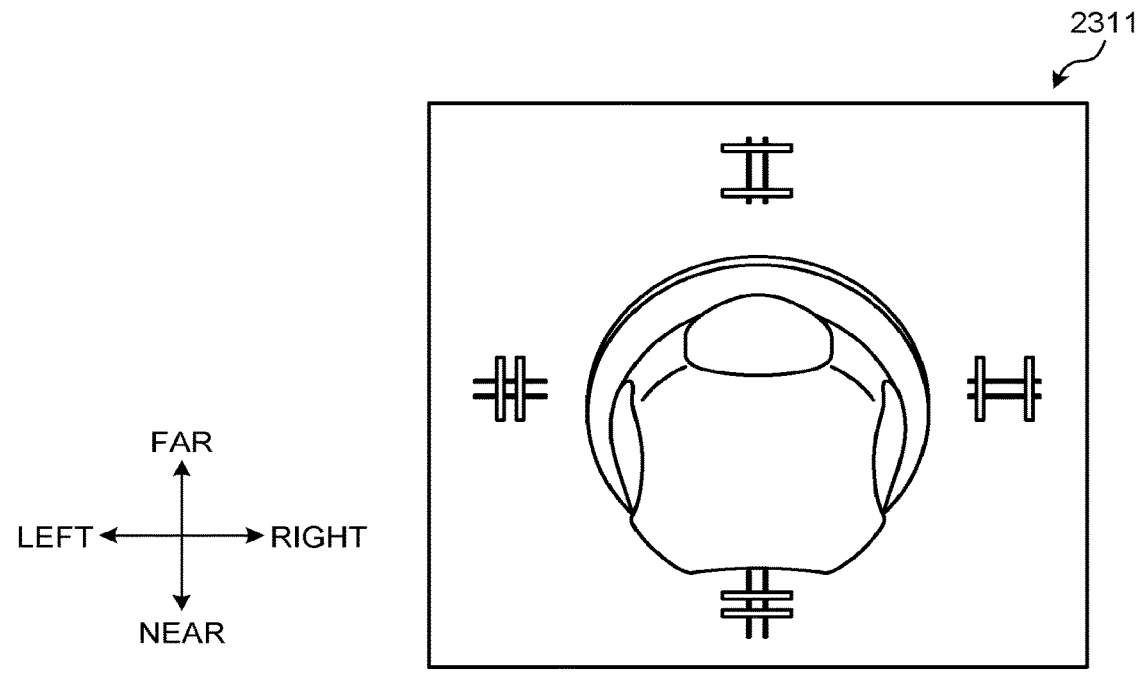
FIG. 4 is a diagram illustrating an example of the console according to the first embodiment.

For example, as illustrated in FIG. 4, the significance of each direction of inclination is displayed around the diaphragm blade stick 2311. That is, when the operator performs an operation to incline the diaphragm blade stick 2311 toward the far side, the acquisition function 241 moves the upper diaphragm blade 131a and the lower diaphragm blade 131b in such a way that the distance therebetween increases. Alternatively, when the operator performs an operation to incline the diaphragm blade stick 2311 toward the near side, the acquisition function 241 moves the upper diaphragm blade 131a and the lower diaphragm blade 131b in such a way that the distance therebetween decreases. Herein, FIG. 4 is a diagram illustrating an example of the console according to the first embodiment.

In an identical manner, when the operator performs an operation to incline the diaphragm blade stick 2311 toward the left side, the acquisition function 241 moves the left-side diaphragm blade 131c and the right-side diaphragm blade 131d in such a way that the distance therebetween decreases. Alternatively, when the operator performs an operation to incline the diaphragm blade stick 2311 toward the right side, the acquisition function 241 moves the left-side diaphragm blade 131c and the right-side diaphragm blade 131d in such a way that the distance therebetween increases.

The filter sticks 2312a, 2312b, and 2312c are lever-shaped operating units that are inclinable in arbitrary directions or predetermined directions, and that receive an inclination operation from the operator. When the filter sticks 2312a, 2312b, and 2312c are operated by the operator, the acquisition function 241 moves or rotates the compensating filters of the first X-ray limiter 13 according to the direction of inclination.

Figure 5:
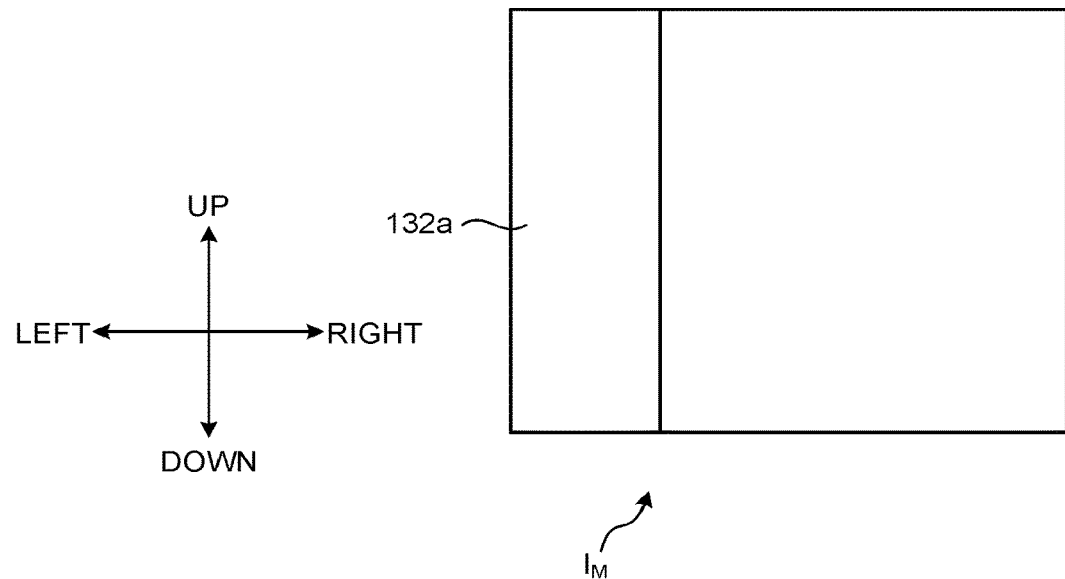
FIGS. 5 to 7 are diagrams for explaining the arrangement of compensating filters according to the first embodiment.
Figure 6:
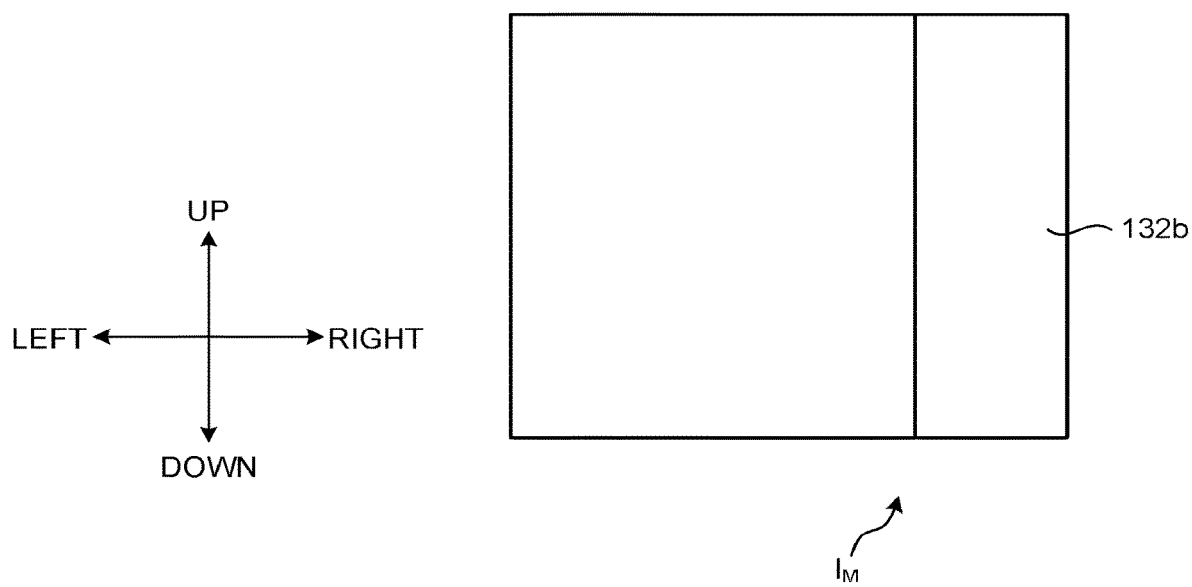
Figure 7:
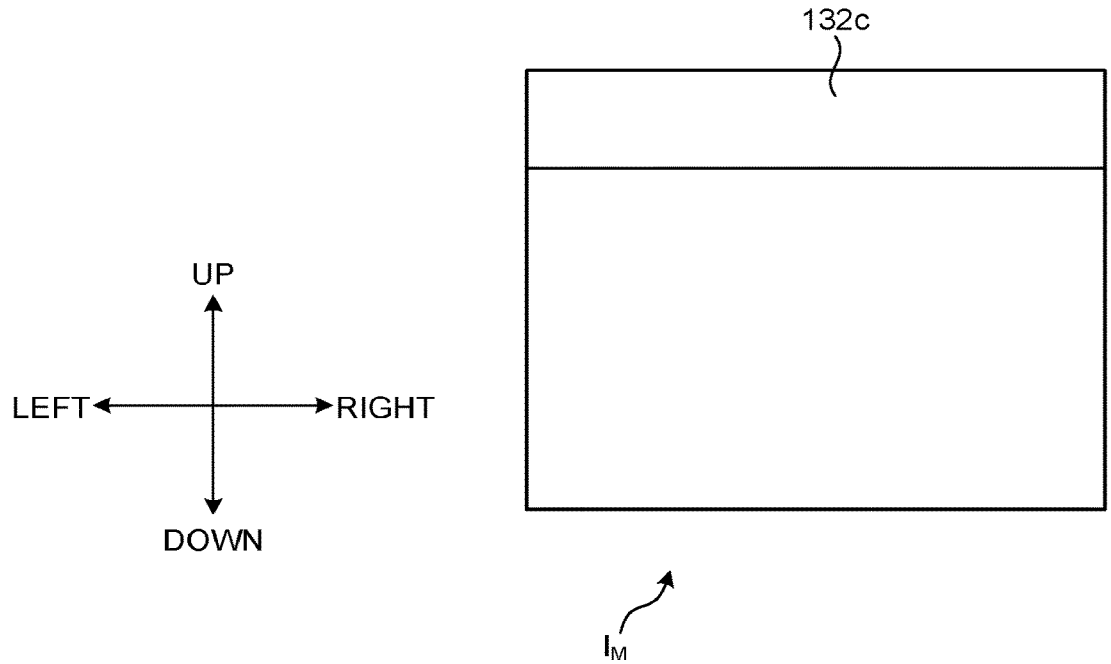

For example, the first X-ray limiter 13 includes three compensating filters 132a, 132b, and 132c. As an example, the compensating filter 132a has the reference position in an external area not included in the X-ray irradiation area, and is configured to be capable of performing translational movement. In the case of controlling the distribution of the X-ray radiation dose using the compensating filter 132a; the compensating filter 132a performs translational movement in the rightward direction from the reference position to the X-ray irradiation area and gets inserted onto the X-ray image IM as illustrated in FIG. 5. That is, the compensating filter 132a is a left-side filter that is inserted from the left side with respect to the X-ray image IM displayed in the display 22. Often, the compensating filter 132a representing the left-side filter is used for suppressing the halation generated in the left-side area of the X-ray image IM. In an identical manner, as illustrated in FIG. 6, the compensating filter 132b is a right-side filter inserted from the right side with respect to the X-ray image IM displayed in the display 22. Moreover, as illustrated in FIG. 7, the compensating filter 132c is an upper-side filter inserted from the upper side with respect to the X-ray image IM displayed in the display 22. Herein, FIGS. 5, 6, and 7 are diagrams for explaining the arrangement of the compensating filters according to the first embodiment.

Figure 8:
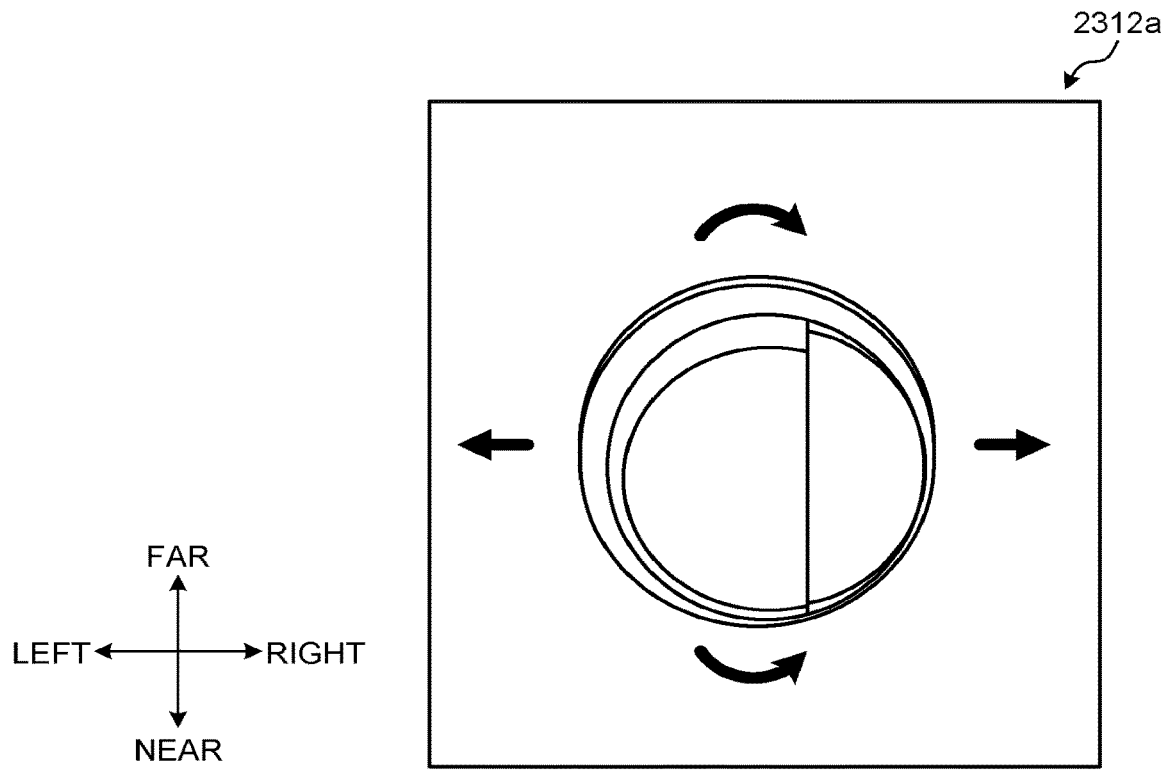
FIG. 8 is a diagram illustrating an example of the console according to the first embodiment.

For example, when the filter stick 2312a is operated by the operator; the acquisition function 241 controls the movement of the compensating filter 132a according to the direction of inclination of the filter stick 2312a. As illustrated in FIG. 8, the significance of each direction of inclination is displayed around the filter stick 2312a. Herein, FIG. 8 is a diagram illustrating an example of the console according to the first embodiment.

Figure 9:
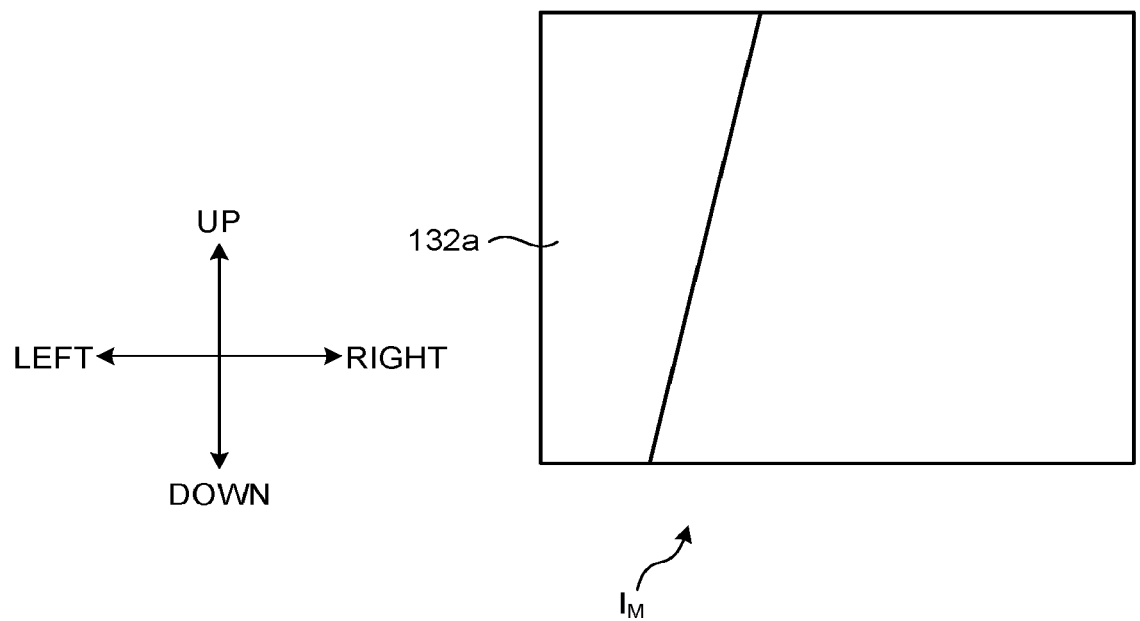
FIGS. 9 to 12 are diagrams for explaining the arrangement of the compensating filters according to the first embodiment.
Figure 10:
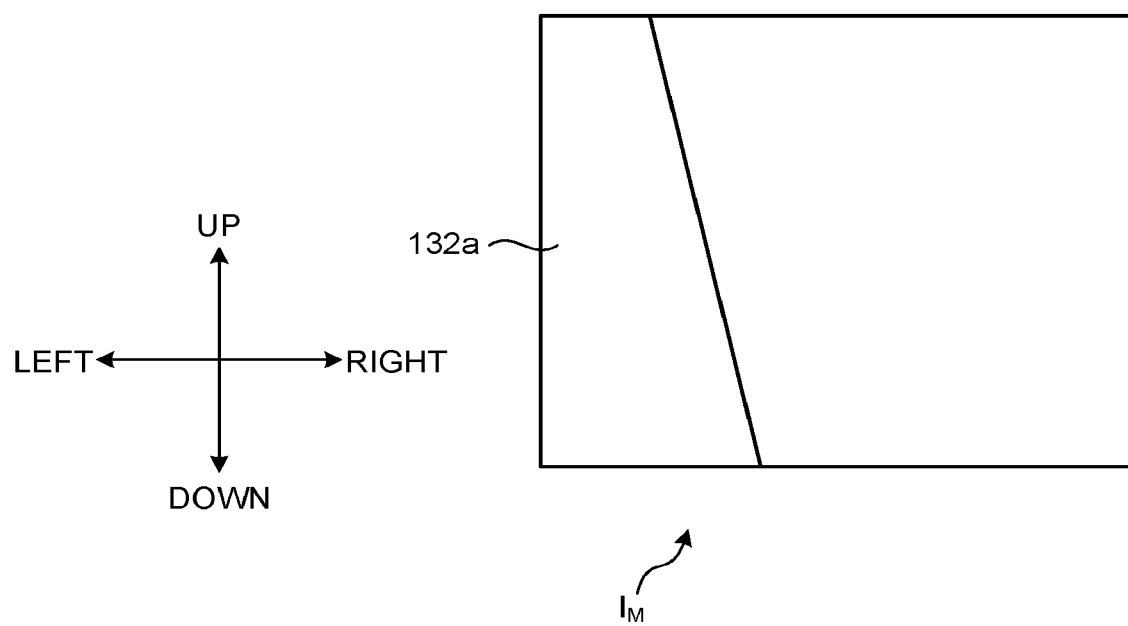
Figure 11:
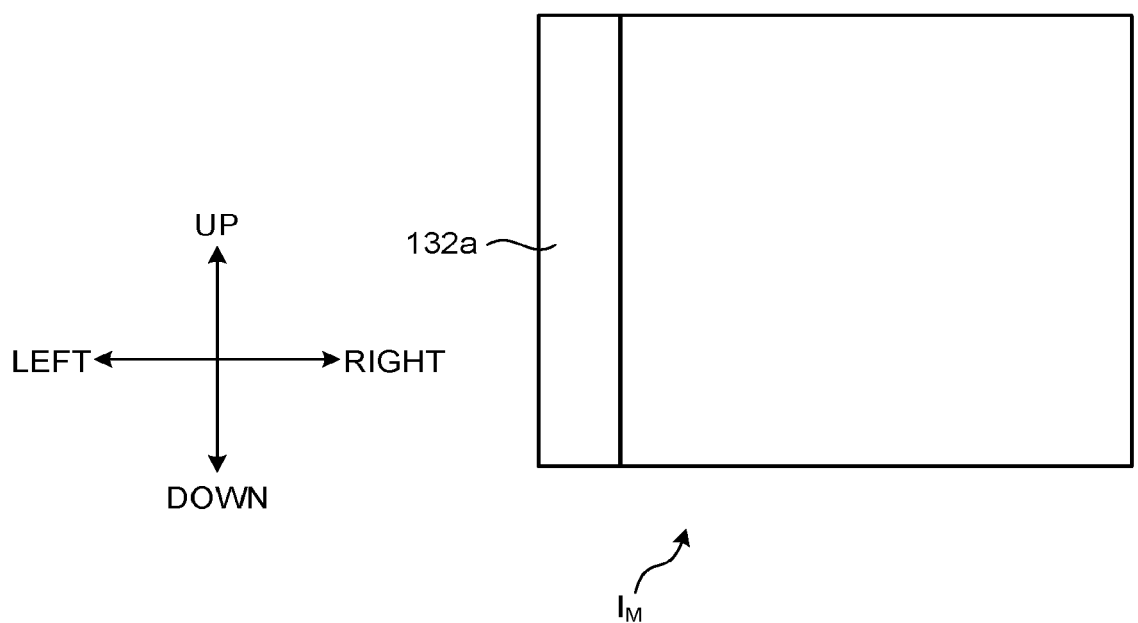
Figure 12:
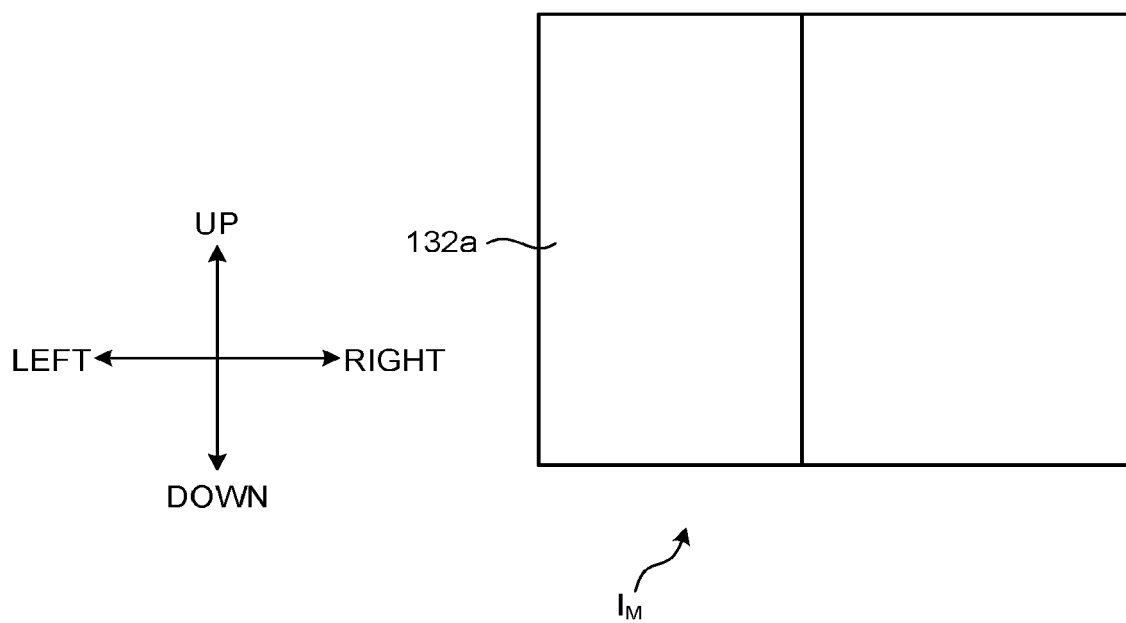

For example, when the operator performs an operation to incline the filter stick 2312a toward the far side; as illustrated in FIG. 9, the acquisition function 241 rotates the compensating filter 132a in the clockwise direction with respect to the X-ray image IM displayed in the display 22. Alternatively, when the operator performs an operation to incline the filter stick 2312a toward the near side; as illustrated in FIG. 10, the acquisition function 241 rotates the compensating filter 132a in the counterclockwise direction with respect to the X-ray image IM displayed in the display 22. Still alternatively, when the operator performs an operation to incline the filter stick 2312a toward the left side; as illustrated in FIG. 11, the acquisition function 241 moves the compensating filter 132a in the left-hand direction of the X-ray image IM displayed in the display 22. Still alternatively, when the operator performs an operation to incline the filter stick 2312a toward the right side; as illustrated in FIG. 12, the acquisition function 241 moves the compensating filter 132a in the right-hand direction of the X-ray image IM displayed in the display 22. Herein, FIGS. 9 to 12 are diagrams for explaining the arrangement of the compensating filters according to the first embodiment. With reference to FIGS. 5, 6, 7, 9, 10, 11, and 12; although a single filter is inserted in the X-ray irradiation field, it is also possible to simultaneously insert the compensating filters 132a, 132b, and 132c in the X-ray irradiation field.

When the operator performs an operation to incline the filter stick 2312b toward the far side, the acquisition function 241 rotates the compensating filter 132b in the counterclockwise direction with respect to the X-ray image IM displayed in the display 22. Alternatively, when the operator performs an operation to incline the filter stick 2312b toward the near side, the acquisition function 241 rotates the compensating filter 132b in the clockwise direction with respect to the X-ray image IM displayed in the display 22. Still alternatively, when the operator performs an operation to incline the filter stick 2312b toward the left side, the acquisition function 241 moves the compensating filter 132b in the left-hand direction of the X-ray image IM displayed in the display 22. Still alternatively, when the operator performs an operation to incline the filter stick 2312b toward the right side, the acquisition function 241 moves the compensating filter 132b in the right-hand direction of the X-ray image IM displayed in the display 22.

When the operator performs an operation to incline the filter stick 2312c toward the far side, the acquisition function 241 rotates the compensating filter 132c in the clockwise direction with respect to the X-ray image IM displayed in the display 22. Alternatively, when the operator performs an operation to incline the filter stick 2312c toward the near side, the acquisition function 241 rotates the compensating filter 132c in the counterclockwise direction with respect to the X-ray image IM displayed in the display 22. Still alternatively, when the operator performs an operation to incline the filter stick 2312c toward the left side, the acquisition function 241 moves the compensating filter 132c in the upward direction with respect to the X-ray image IM displayed in the display 22. Still alternatively, when the operator performs an operation to incline the filter stick 2312c toward the right side, the acquisition function 241 moves the compensating filter 132c in the downward direction with respect to the X-ray image IM displayed in the display 22.

As described above, the four diaphragm blades (the diaphragm blades 131a, 131b, 131c, and 131d) and the three compensating filters (the compensating filters 132a, 132b, and 132c) of the first X-ray limiter 13 can be operated using the diaphragm operation console 231 illustrated in FIG. 2. In an identical manner, if the arm switching button 2313b is operated, the four diaphragm blades and the three compensating blades of the second X-ray limiter 17 can be operated.

However, in the case of using the diaphragm operation console 231, it is not possible to intuitively understand the operations that need to be performed in order to adjust the arrangement of the diaphragm blades. For example, with reference to FIG. 4, "the operation of inclining the diaphragm blade stick 2311 toward the far side" is associated to "the operation of increasing the distance between the upper diaphragm blade 131a and the lower diaphragm blade 131b". However, that relationship is not intuitively understandable. That is, when the diaphragm blade stick 2311 is inclined toward the far side, it is not possible to determine, with the senses, whether the distance between the upper diaphragm blade 131a and the lower diaphragm blade 131b increases or decreases. Hence, at the time of adjusting the arrangement of the diaphragm blades using the diaphragm operation console 231, it requires time and efforts to refer to the surrounding display of the diaphragm blade stick 2311, and that may sometimes hinder the procedure.

Regarding the compensating filters too, in an identical manner, in the case of using the diaphragm operation console 231, it is not possible to intuitively understand the operations that need to be performed in order to adjust the arrangement of the compensating filters. For example, with reference to FIG. 8, "the operation of inclining the filter stick 2312a toward the far side" is associated to "the operation of rotating the compensating filter 132a in the clockwise direction". However, that relationship is not intuitively understandable. That is, when the filter stick 2312a is inclined toward the far side, it is not possible to determine, with the senses, whether the compensating filter 132a rotates in the clockwise direction or the counterclockwise direction or whether the compensating filter 132a moves around. Hence, at the time of adjusting the arrangement of the compensating filter 132a using the diaphragm operation console 231, it requires time and efforts to refer to the surrounding display of the filter stick 2312a, and that may sometimes hinder the procedure.

Figure 13:
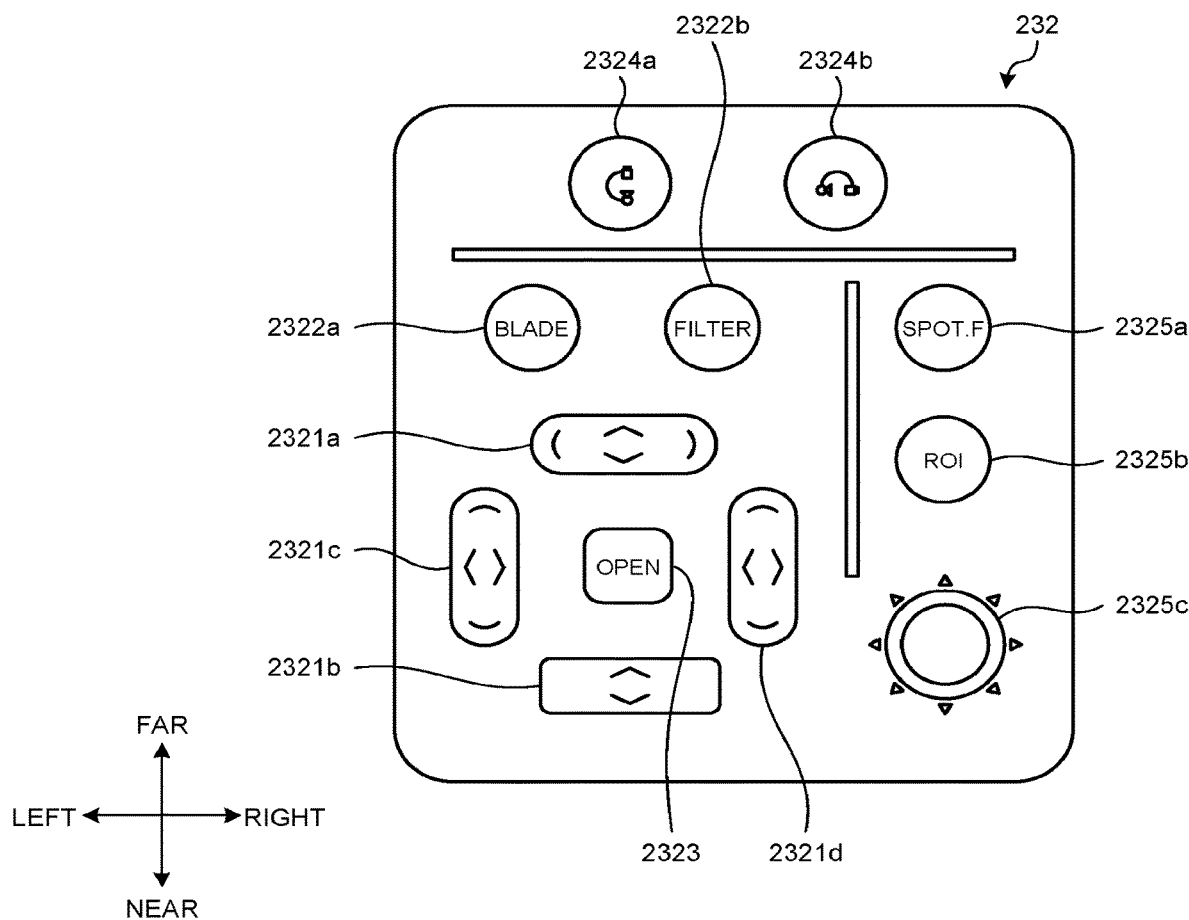
FIG. 13 is a diagram illustrating an example of the console according to the first embodiment.

In that regard, in the X-ray diagnosis apparatus 1, a diaphragm operation console 232 illustrated in FIG. 13 enables intuitive operations with respect to the diaphragm blades and the compensating filters, and enables achieving enhancement in the operability related to the diaphragm blades and the compensating filters. FIG. 13 is a diagram illustrating an example of the console according to the first embodiment. The diaphragm operation console 232 is installed, for example, on the bed on which the subject P lies down. As an example, the diaphragm operation console 232 is installed laterally on the bed.

As illustrated in FIG. 13, the diaphragm operation console 232 has the following components installed therein: a far-side stick 2321a; a near-side stick 2321b; a left-side stick 2321c; a right-side stick 2321d; switching buttons 2322a and 2322b; an open button 2323; arm switching buttons 2324a and 2324b; fluoroscopy mode switching buttons 2325a and 2325b; and an operation stick 2325c. FIG. 13 is a diagram in which the diaphragm operation console 232 is viewed while facing it. With reference to FIG. 13, the operator operates the diaphragm operation console 232 from the lower side. That is, when viewed from the side of the operator; the far side, the near side, the left side, and the right side can be defined as illustrated in FIG. 13. Moreover, when the diaphragm operation console 232 is installed on the bed, the tabletop 20 is on the far side of the diaphragm operation console 232.

When the diaphragm operation console 232 is installed on the bed, the directions in the far side, the near side, the left side, and the right side can be defined with reference to the bed. For example, when the diaphragm operation console 232 is laterally installed on the bed, the directions in the far side, the near side, the left side, and the right side can be defined from that side of the two sides of the bed on which the diaphragm operation console 232 is installed.

The arm switching buttons 2324a and 2324b are switches for switching between receiving operations with respect to the first X-ray limiter 13 and receiving operations with respect to the second X-ray limiter 17. For example, when the arm switching button 2324a is operated, the acquisition function 241 sets the first X-ray limiter 13, which is held by the first arm 15, as the operation target. Then, while the first X-ray limiter 13 is set as the operation target, if an operating unit such as the stick 2321a or the open button 2323 is operated, the acquisition function 241 controls the operation of the first X-ray limiter 13 according to the received input operation. In an identical manner, when the arm switching button 2324b is operated, the acquisition function 241 sets the second X-ray limiter 17, which is held by the second arm 19, as the operation target. The following explanation is given about the case in which the first X-ray limiter 13 is set as the operation target.

The switching buttons 2322a and 2322b enable switching between a diaphragm mode in which the diaphragm blades are operated and a filter mode in which the compensating filters are operated. For example, the acquisition function 241 sets the diaphragm mode when the switching button 2322a indicated by "BLADE" is operated, and sets the filter mode when the switching button 2322b indicated by "FILTER" is operated.

For example, when the diaphragm mode is set; the far-side stick 2321a, the near-side stick 2321b, the left-side stick 2321c, and the right-side stick 2321d receive operations with respect to the four diaphragm blades. Herein, the sticks 2321a, 2321b, 2321c, and 2321d represent examples of four physical operating units. The far-side stick 2321a represents an example of a far-side operating unit. The near-side stick 2321b represents an example of a near-side operating unit. The left-side stick 2321c represents an example of a left-side operating unit. The right-side stick 2321d represents an example of a right-side operating unit. As illustrated in FIG. 13, on the diaphragm operation console 232, the four physical operating units are arranged in four directions. For example, when the diaphragm mode is set; the far-side stick 2321a, the near-side stick 2321b, the left-side stick 2321c, and the right-side stick 2321d receive operations with respect to the diaphragm blades 131a, 131b, 131c, and 131d, respectively. In other words, in the diaphragm mode, operations with respect to the four diaphragm blades are assigned to the four physical operating units.

Figure 14:
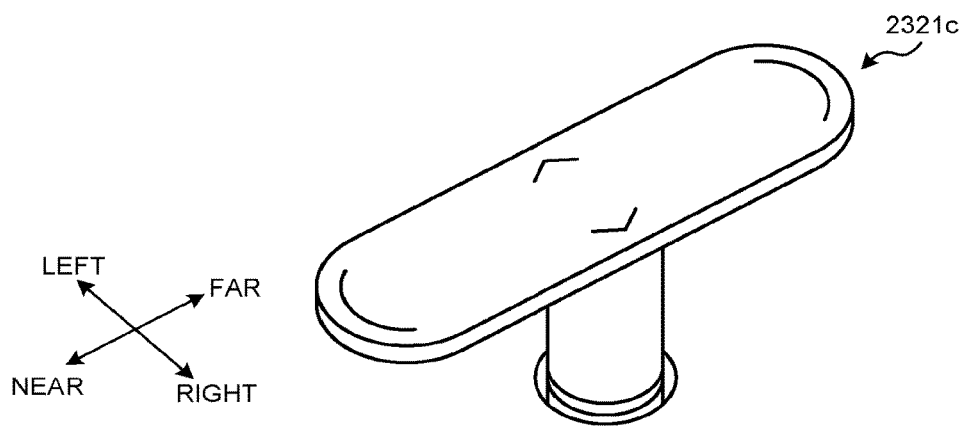
FIG. 14 is a diagram illustrating an example of a left-side operating unit according to the first embodiment.

Explained below with reference to FIG. 14 are the operations performed with respect to the left-side stick 2321c when the diaphragm mode is set. FIG. 14 is a diagram illustrating an example of the left-side operating unit according to the first embodiment. As illustrated in FIG. 14, the left-side stick 2321c is a lever-shaped operating unit that is substantially perpendicular with respect to the directions in the far side, the near side, the left side, and the right side; and that can be inclined in arbitrary directions or predetermined directions. For example, the left-side stick 2321c can be inclined at least in the leftward direction and the rightward direction, and receives inclination operations from the operator for inclination in the leftward direction or the rightward direction. As illustrated in FIG. 14, the left-side stick 2321c has a plate-like member at the leading end thereof, with the far-side/near-side direction serving as the long direction and the leftward/rightward direction serving as the short direction.

When the operator operates the left-side stick 2321c, the acquisition function 241 moves the left-side diaphragm blade 131c of the first X-ray limiter 13 according to the received operation. For example, when an operation of inclining the stick 2321c in the leftward direction is received, the acquisition function 241 moves the diaphragm blade 131c in the leftward direction of the X-ray image IM displayed in the display 22. That is, an operation of inclining the stick 2321c in the leftward direction results in the movement of the diaphragm blade 131c in the leftward direction of the X-ray image IM displayed in the display 22. Alternatively, for example, when an operation of inclining the stick 2321c in the rightward direction is received, the acquisition function 241 moves the diaphragm blade 131c in the rightward direction of the X-ray image IM displayed in the display 22. That is, an operation of inclining the stick 2321c in the rightward direction results in the movement of the diaphragm blade 131c in the rightward direction of the X-ray image IM displayed in the display 22.

Herein, the stick 2321c is placed on the left side of the sticks 2321a, 2321b, and 2321d, and it is thus intuitively easy to understand that the stick 2321c corresponds to the diaphragm blade 131c. Moreover, since the stick 2321c has the shape in which the far-side/near-side direction is the long direction, it is further intuitively easy to understand that the stick 2321c corresponds to the left-side contour of the X-ray irradiation area of the X-ray image IM, that is, corresponds to the left-side diaphragm blade 131c. Furthermore, it is also intuitively easy to understand that an operation of inclining the stick 2321c in the leftward direction results in the movement of the diaphragm blade 131c in the leftward direction and that an operation of inclining the stick 2321c in the rightward direction results in the movement of the diaphragm blade 131c in the rightward direction. That is, the stick 2321c enables intuitive operations with respect to the diaphragm blade 131c and enables achieving enhancement in the operability related to the diaphragm blade 131c.

In an identical manner, the sticks 2321a, 2321b, and 2321d are lever-shaped operating units that are substantially perpendicular with respect to the directions in the far side, the near side, the left side, and the right side; and that can be inclined in arbitrary directions or predetermined directions. For example, the far-side stick 2321a can be inclined at least in the far-side direction and the near-side direction, and receives inclination operations from the operator for inclination in the far-side direction and the near-side direction. The near-side stick 2321a can be inclined at least in the far-side direction and the near-side direction, and receives inclination operations from the operator for inclination in the far-side direction and the near-side direction. The right-side stick 2321d can be inclined at least in the leftward direction and the rightward direction, and receives inclination operations from the operator for inclination in the rightward direction and the leftward direction.

The far-side stick 2321a has a plate-like member at the leading end thereof, with the leftward/rightward direction serving as the long direction and the far-side/near-side direction serving as the short direction. The near-side stick 2321b has a plate-like member at the leading end thereof, with the leftward/rightward direction serving as the long direction and the far-side/near-side direction serving as the short direction. The right-side stick 2321d has a plate-like member at the leading end thereof, with the far-side/near-side direction serving as the long direction and the leftward/rightward direction serving as the short direction. As illustrated in FIG. 13, the shape of the plate-like member of the stick 2321b is different than the shape of the plate-like members of the sticks 2321a, 2321c, and 2321d. Regarding that, the explanation is given later.

For example, when the operator operates the far-side stick 2321a, the acquisition function 241 controls the movement of the upper diaphragm blade 131a of the first X-ray limiter 13 according to the received operation. For example, when an operation of inclining the stick 2321a in the far-side direction is received, the acquisition function 241 moves the diaphragm blade 131a in the upward direction of the X-ray image IM displayed in the display 22. That is, an operation of inclining the stick 2321a in the far-side direction results in the movement of the diaphragm blade 131a in the upward direction of the X-ray image IM displayed in the display 22. Alternatively, when an operation of inclining the stick 2321a in the near-side direction is received, the acquisition function 241 moves the diaphragm stick 131a in the downward direction of the X-ray image IM displayed in the display 22. That is, an operation of inclining the stick 2321a in the near-side direction results in the movement of the diaphragm blade 131a in the downward direction of the X-ray image IM displayed in the display 22.

The stick 2321a is placed on the far side of the sticks 2321b, 2321c, and 2321d, and thus it is intuitively easy to understand that the stick 2321a corresponds to the diaphragm blade 131a. Moreover, it is also intuitively easy to understand that an operation of including the stick 2321a in the far-side direction results in the movement of the diaphragm blade 131a in the upward direction and that an operation of inclining the stick 2321a in the near-side direction results in the movement of the diaphragm blade 131a in the downward direction. That is, the stick 2321a enables intuitive operations with respect to the diaphragm blade 131a and enables achieving enhancement in the operability related to the diaphragm blade 131a.

In an identical manner, when the operator operates the near-side stick 2321b, the acquisition function 241 controls the movement of the lower diaphragm blade 131b of the first X-ray limiter 13 according to the received operation. For example, as a result of an operation of inclining the stick 2321b in the far-side direction, the diaphragm blade 131b moves in the upward direction of the X-ray image IM displayed in the display 22. Moreover, as a result of an operation of inclining the stick 2321b in the near-side direction, the diaphragm blade 131b moves in the downward direction of the X-ray image IM displayed in the display 22.

The stick 2321b is placed on the near side of the sticks 2321b, 2321a, and 2321c; and thus it is intuitively easy to understand that the stick 2321b corresponds to the lower diaphragm blade 131b. Moreover, it is also intuitively easy to understand that an operation of inclining the stick 2321b in the far-side direction results in the movement of the diaphragm blade 131b in the upward direction and that an operation of inclining the stick 2321b in the near-side direction results in the movement of the diaphragm blade 131b in the downward direction. That is, the stick 2321b enables intuitive operations with respect to the diaphragm blade 131b and enables achieving enhancement in the operability related to the diaphragm blade 131b.

In an identical manner, when the operator operates the right-side stick 2321d, the acquisition function 241 controls the movement of the right-side diaphragm blade 131d of the first X-ray limiter 13 according to the received operation. For example, an operation of inclining the stick 2321d in the leftward direction results in the movement of the diaphragm blade 131d in the leftward direction of the X-ray image IM displayed in the display 22. Alternatively, an operation of inclining the stick 2321d in the rightward direction results in the movement of the diaphragm blade 131d in the rightward direction of the X-ray image IM displayed in the display 22.

The stick 2321d is placed on the right side of the sticks 2321a, 2321b, and 2321c; and thus it is intuitively easy to understand that the stick 2321d corresponds to the right-side diaphragm blade 131d. Moreover it is also intuitively easy to understand that an operation of inclining the stick 2321d in the leftward direction results in the movement of the diaphragm blade 131d in the leftward direction and that an operation of inclining the stick 2321d in the rightward direction results in the movement of the diaphragm blade 131d in the rightward direction. That is, the stick 2321d enables intuitive operations with respect to the diaphragm blade 131d and enables achieving enhancement in the operability related to the diaphragm blade 131d.

Given below is the explanation of the case in which the filter mode is set. When the filter mode is set, the left-side stick 2321c as well as the right-side stick 2321d receives operations with respect to the compensating filters 132a and 132b. Moreover, the far-side stick 2321a receives operations with respect to the compensating filter 132c. In other words, in the filter mode, operations with respect to three compensating filters are assigned to the four physical operating units.

For example, the sticks 2321c, 2321d, and 2321a are further configured to be rotatable in the clockwise direction and the counterclockwise direction. As an example, the stick 2321c is inclinable in at least the leftward direction and the rightward direction, and is further configured to be rotatable with the direction substantially perpendicular to the far-side/near-side direction and the leftward/rightward direction serving as the rotation axis. The direction substantially perpendicular to the far-side/near-side direction and the leftward/rightward direction implies, for example, the vertical direction or the direction perpendicular to the top face of the diaphragm operation console 232 (i.e., the face illustrated in FIG. 13). For example, when performing an operation of rotating the stick 2321c, the operator holds and twists the stick 2321c and rotates it.

While the filter mode is set, when the stick 2321c is operated, the acquisition function 241 controls the movement and the rotation of the compensating filter 132a according to the received operation. For example, when an operation of inclining the stick 2321c in the leftward direction is received, the acquisition function 241 moves the compensating filter 132a in the leftward direction of the X-ray image IM displayed in the display 22. That is, an operation of inclining the stick 2321c in the leftward direction results in the movement of the compensating filter 132a in the leftward direction of the X-ray image IM displayed in the display 22. Alternatively, for example, when an operation of inclining the stick 2321c in the rightward direction is received, the acquisition function 241 moves the compensating filter 132a in the leftward direction of the X-ray image IM displayed in the display 22. That is, an operation of inclining the stick 2321c in the rightward direction results in the movement of the compensating filter 132a in the rightward direction of the X-ray image IM displayed in the display 22.

Still alternatively, for example, when an operation of rotating the stick 2321c in the clockwise direction is received, the acquisition function 241 rotates the compensating filter 132a in the clockwise direction with respect to the X-ray image IM displayed in the display 22. That is, an operation of rotating the stick 2321c in the clockwise direction results in the rotation of the compensating filter 132a in the clockwise direction with respect to the X-ray image IM displayed in the display 22. Still alternatively, for example, when an operation of rotating the stick 2321c in the counterclockwise direction is received, the acquisition function 241 rotates the compensating filter 132a in the counterclockwise direction with respect to the X-ray image IM displayed in the display 22. That is, an operation of inclining the stick 2321c in the counterclockwise direction results in the rotation of the compensating filter 132a in the counterclockwise direction with respect to the X-ray image IM displayed in the display 22.

The compensating filter 132a is the left-side filter that is inserted from the left side with respect to the X-ray image IM displayed in the display 22. Thus, it is intuitively easy to understand that the stick 2321c, which is placed on the left side of the sticks 2321a, 2321b, and 2321d, corresponds to the compensating filter 132a representing the left-side filter. Moreover, it is also intuitively easy to understand that an operation of inclining the stick 2321c in the leftward direction results in the movement of the compensating filter 132a in the leftward direction and that an operation of inclining the stick 2321c in the rightward direction results in the movement of the compensating filter 132a in the rightward direction. Furthermore, it is also intuitively easy to understand that an operation of rotating the stick 2321c in the clockwise direction results in the clockwise rotation of the compensating filter 132a and that an operation of rotating the stick 2321c in the counterclockwise direction results in the counterclockwise rotation of the compensating filter 132a. That is, the stick 2321c enables intuitive operations with respect to the compensating filter 132a and enables achieving operability related to the compensating filter 132a.

In an identical manner, the stick 2321d is inclinable in at least the leftward direction and the rightward direction, and is further configured to be rotatable with the direction substantially perpendicular to the far-side/near-side direction and the leftward/rightward direction serving as the rotation axis. When the stick 2321d is operated, the acquisition function 241 controls the movement and the rotation of the compensating filter 132b according to the received operation. For example, an operation of inclining the stick 2321d in the leftward direction results in the movement of the compensating filter 132a in the leftward direction of the X-ray image IM displayed in the display 22. Alternatively, an operation of inclining the stick 2321d in the rightward direction results in the movement of the compensating filter 132a in the rightward direction of the X-ray image IM displayed in the display 22. Still alternatively, an operation of rotating the stick 2321d in the clockwise direction results in the rotation of the compensating filter 132b in the clockwise direction with respect to the X-ray image IM displayed in the display 22. Still alternatively, an operation of rotating the stick 2321d in the counterclockwise direction results in the rotation of the compensating filter 132b in the counterclockwise direction with respect to the X-ray image IM displayed in the display 22.

The compensating filter 132b is a right-side filter that is inserted from the right side with respect to the X-ray image IM displayed in the display 22. Thus, it is intuitively easy to understand that the stick 2321d, which is placed on the right side of the sticks 2321a, 2321b, and 2321c, corresponds to the compensating filter 132b representing the right-side filter. Moreover, it is also intuitively easy to understand that an operation of inclining the stick 2321d in the leftward direction results in the movement of the compensating filter 132b in the leftward direction and that an operation of inclining the stick 2321d in the rightward direction results in the movement of the compensating filter 132b in the rightward direction. Furthermore, it is also intuitively easy to understand that an operation of rotating the stick 2321d in the clockwise direction results in the clockwise rotation of the compensating filter 132b and that an operation of rotating the stick 2321d in the counterclockwise direction results in the counterclockwise rotation of the compensating filter 132b. That is, the stick 2321d enables intuitive operations with respect to the compensating filter 132b and enables achieving enhancement in the operability related to the compensating filter 132b.

In an identical manner, the stick 2321a is inclinable at least in the far-side direction and the near-side direction, and is further configured to be rotatable with the direction substantially perpendicular to the far-side/near-side direction and the leftward/rightward direction serving as the rotation axis. When the stick 2321a is operated, the acquisition function 241 controls the movement and the rotation of the compensating filter 132c according to the received operation. For example, an operation of inclining the stick 2321a in the far-side direction results in the movement of the compensating filter 132c in the upward direction of the X-ray image IM displayed in the display 22. Alternatively, an operation of inclining the stick 2321a in the near-side direction results in the movement of the compensating filter 132c in the downward direction of the X-ray image IM displayed in the display 22. Still alternatively, an operation of rotating the stick 2321a in the clockwise direction results in the rotation of the compensating filter 132c in the clockwise direction with respect to the X-ray image IM displayed in the display 22. Still alternatively, an operation of rotating the stick 2321a in the counterclockwise direction results in the rotation of the compensating filter 132c in the counterclockwise direction with respect to the X-ray image IM displayed in the display 22.

The compensating filter 132c is an upper-side filter that is inserted from the upper side with respect to the X-ray image IM displayed in the display 22. Thus, it is intuitively easy to understand that the stick 2321a, which is placed on the far side of the sticks 2321b, 2321c, and 2321d, corresponds to the compensating filter 132c representing the upper-side filter. Moreover, it is also intuitively easy to understand that an operation of inclining the stick 2321a in the far-side direction results in the movement of the compensating filter 132c in the upward direction and that an operation of inclining the stick 2321a in the near-side direction results in the movement of the compensating filter 132c in the downward direction. Furthermore, it is also intuitively easy to understand that an operation of rotating the stick 2321a in the clockwise direction results in the clockwise rotation of the compensating filter 132c and that an operation of rotating the stick 2321a in the counterclockwise direction results in the counterclockwise rotation of the compensating filter 132c. That is, the stick 2321a enables intuitive operations with respect to the compensating filter 132c and enables achieving enhancement in the operability related to the compensating filter 132c.

As far as the four operating units are concerned, the operating units corresponding to compensating filters can be configured to have a different shape than the operating units not corresponding to compensating filters. For example, as illustrated in FIG. 13, the stick 2321a corresponding to the compensating filter 132a, the stick 2321d corresponding to the compensating filter 132b, and the stick 2321a corresponding to the compensating filter 132c can be configured to have a different shape than the stick 2321b not corresponding to any compensating filter.

More particularly, when the diaphragm operation console 232 is viewed while facing it as illustrated in FIG. 13, the sticks 2321a, 2321d, and 2321a corresponding to compensating filters are configured to have the outer periphery made of two straight lines and two curved lines. On the other hand, when the diaphragm operation console 232 is viewed while facing it, the stick 2321b not corresponding to any compensating filter is configured to have the outer periphery made of four straight lines and four curved lines that join the straight lines. The length of the four curved lines in the outer periphery of the stick 2321b is kept shorter than the shortest straight line from among the four straight lines in the same outpour periphery.

In this way, as compared to the stick 2321b that does not correspond to any compensating filter; the sticks 2321a, 2321d, and 2321a corresponding to compensating filters have a higher ratio of curved lines constituting the outer periphery and have the shape close to an ellipse. In contrast, the stick 2321b not corresponding to any compensating filter has a higher ratio of straight lines and has the shape close to a quadrangle. As compared to a quadrangle, an ellipse is ideationally easier to be tied to "rotation". Hence, the operator becomes able to intuitively understand that the sticks 2321c, 2321d, and 2321a are rotatable and represent operating units corresponding to compensating filters. Moreover, since the operating units corresponding to compensating filters have a different shape than the operating units not corresponding to compensating filters; the operator becomes able to understand, even without looking, for example, whether the operator unit that he or she is touching is an operating unit corresponding to a compensating filter. Furthermore, instead of giving a simple quadrangular shape to the stick 2321b, since the shape has a combination of straight lines and curved lines; the corner portions of the quadrangle are eliminated thereby preventing jamming of fingers of the operator at the corner portions.

With reference to FIG. 13, the explanation is given about the case in which the operating units corresponding to compensating filters have a different shape than the operating units not corresponding to compensating filters. However, the embodiment is not limited by that case. That is, in the diaphragm operation console 232, the operating units corresponding to the compensating filters and the operating units not corresponding to the compensating filters can be different from each other in aspects other than the shape. For example, the operating units corresponding to the compensating filters and the operating units not corresponding to the compensating filters can be different from each other in the color, in the design pattern, or in the texture either in place of the shape or in addition to the shape. Apart from that, for example, using an arbitrary method such as illuminating only the operating units corresponding to compensating filters so as to enable the operator to recognize those operating units, it is possible to differentiate the operating units corresponding to compensating filters from the operating units not corresponding to compensating filters.

The open button 2323 is meant for causing retraction of the four diaphragm blades all at once. For example, when the operator operates the open button 2323; the acquisition function 241 causes retraction of the diaphragm blades 131a, 131b, 131c, and 131d all at once to an external area excluded from the X-ray irradiation area. As an example, when the open button 2323 is operated, the acquisition function 241 moves the diaphragm blade 131a in the upward direction with respect to the X-ray image IM displayed in the display 22; moves the diaphragm blade 131b in the downward direction with respect to the X-ray image IM displayed in the display 22; moves the diaphragm blade 131c in the leftward direction with respect to the X-ray image IM displayed in the display 22; moves the diaphragm blade 131d in the rightward direction with respect to the X-ray image IM displayed in the display 22; and thus causes retraction of the four diaphragm blades all at once. That is, when the open button 2323 is operated, the four diaphragm blades that surround the X-ray image IM, which is displayed in the display 22, from four directions are retracted in the four directions to move away from the X-ray image IM.

As illustrated in FIG. 13, the open button 2323 is surrounded by the four operating units (the sticks 2321a, 2321b, 2321c, and 2321d). Moreover, the X-ray image IM that is displayed in the display 22 is surrounded by the four diaphragm blades. In this way, the positional relationship of the open button 2323 with the four operating units is similar to the positional relationship of the X-ray image IM, which is displayed in the display 22, with the four diaphragm blades. Moreover, when the diaphragm operation console 231 is viewed while facing it, the open button 2323 has the outer periphery made of four straight lines and four curved lines that join the straight lines. The length of the four curved lines in the outer periphery of the open button 2323 is kept shorter than the shortest straight line from among the four straight lines in the same outpour periphery. That is, the open button 2323 has the shape close to a quadrangular. In this way, it is intuitively easy to understand that an operation of the open button 2323 causes retraction of the four diaphragm blades in four directions. That is, the open button 2323 enables intuitive operations with respect to the four diaphragm blades.

Moreover, instead of giving a simple quadrangular shape to the open button 2323, since the shape has a combination of straight lines and curved lines; the corner portions of the quadrangle are eliminated thereby preventing jamming of fingers of the operator at the corner portions. Moreover, as a result of placing the open button 2323 at a position surrounded by the sticks 2321a, 2321b, 2321c, and 2321d; for example, the open button 2323 can be operated even without looking at it.

Meanwhile, the configuration can be such that, when the open button 2323 is operated, the acquisition function 241 causes retraction of the four diaphragm blades as well as the compensating filters. For example, when the open button 2323 is operated; the acquisition function 241 causes retraction of the compensating filters 132a, 132b, and 132c all at once to the respective reference positions. As an example, when the open button 2323 is operated, the acquisition function 241 makes the compensating filter 132a perform translational movement in the leftward direction with respect to the X-ray image IM displayed in the display 22; makes the compensating filter 132b perform translational movement in the rightward direction with respect to the X-ray image IM displayed in the display 22; makes the compensating filter 132c perform translational movement in the upward direction with respect to the X-ray image IM displayed in the display 22; and thus causes retraction of the three compensating filters all at once.

The fluoroscopy mode switching buttons 2325a and 2325b are switches for switching between fluoroscopy modes. For example, when the fluoroscopy mode switching button 2325a indicated by "SPOT.F" is operated, the acquisition function 241 sets a spot fluoroscopy mode as the fluoroscopy mode. When the fluoroscopy mode switching button 2325b indicated by "ROI (Region Of Interest)" is operated, the acquisition function 241 sets a spot ROI mode as the fluoroscopy mode. Herein, the spot fluoroscopy mode represents an example of a first fluoroscopy mode, and the spot ROI mode represents an example of a second fluoroscopy mode.

Figure 15:
FIGS. 15 and 16 are diagrams illustrating examples of fluoroscopy modes according to the first embodiment.

Explained below with reference to FIG. 15 is the case in which the spot fluoroscopy mode is set. FIG. 15 is a diagram illustrating an example of the fluoroscopy mode according to the first embodiment. In order to set the spot fluoroscopy mode, the operator operates the fluoroscopy mode switching button 2325a as illustrated in FIG. 15, for example.

In the case of performing fluoroscopy in the spot fluoroscopy mode, firstly, the acquisition function 241 obtains at least one X-ray image of the subject P. For example, the operator presses a foot pedal and inputs an instruction for starting X-ray irradiation. Then, the acquisition function 241 starts irradiating the subject P with X-rays and acquires a plurality of X-ray images in chronological order (i.e. a plurality of X-ray images in time series). Then, the control function 242 sequentially displays the acquired X-ray images in the display 22. Subsequently, according to an input operation performed by the operator by referring to the X-ray images that are sequentially displayed in the display 22, the acquisition function 241 obtains the last image hold (LIH). The LIH represents the X-ray images acquired from a wide area including the region of interest of the subject P. The LIH represents an example of the X-ray images acquired in the past. After obtaining the LIH, the acquisition function 241 stops the irradiation of the subject P with the X-rays.

Then, in response to an instruction from the operator, the acquisition function 241 starts spot fluoroscopy. For example, the operator presses the foot pedal and inputs an instruction to start X-ray irradiation. Then, the acquisition function 241 starts irradiating the subject P with X-rays, and acquires a plurality of X-ray images IM in chronological order while controlling the X-ray irradiation area using the four diaphragm blades. The control function 242 sequentially displays the acquired X-ray images IM in the display 22 and displays the LIH.

More particularly, the acquisition function 241 arranges the four diaphragm blades at default positions and starts acquiring the X-ray images IM. As a result, the acquisition function 241 acquires, in chronological order, a plurality of X-ray images IM corresponding to a first area R1 illustrated in a display example D1 in FIG. 15. The control function 242 sequentially displays the acquired X-ray images IM in the first area R1 in the display example D1. Moreover, the control function 242 displays the LIH in a second area R2 that is the surrounding area of the first area R1. That is, the control function 242 displays, in the first area R1, real-time images that are sequentially acquired; and displays, in the second area R2, the past images acquired in the past.

Then, the acquisition function 241 receives an operation from the operator with respect to the first area R1. For example, as illustrated in FIG. 15, the operator operates the operation stick 2325c. Herein, while maintaining the relative positional relationship among the four diaphragm blades, the acquisition function 241 makes the four diaphragm blades perform translational movement according to the operation with respect to the four diaphragm blades. As a result, while maintaining its own shape, the X-ray irradiation area formed by the four diaphragm blades moves with respect to the subject P. That is, while maintaining the shape of the X-ray irradiation area formed by the four diaphragm blades, the operation stick 2325c moves the position of the X-ray irradiation area with respect to the subject P. Moreover, accompanying the movement of the X-ray irradiation area, the first area R1 in which the real-time images are displayed also moves as illustrated in a display example D2 in FIG. 15.

The operation stick 2325c is a lever-shaped operation unit that is inclinable in arbitrary directions or predetermined directions, and receives an inclination operation from the operator. For example, the operation stick 2325c is configured to be inclinable in at least eight directions illustrated by arrows in the display example D2 in FIG. 15.

For example, when an operation to incline the operation stick 2325c in the far side is performed, the acquisition function 241 moves the first area R1 in the upward direction. That is, when an operation to incline the operation stick 2325c in the far side is performed, the acquisition function 241 moves the four diaphragm blades in the upward direction of the X-ray image IM, which is displayed in the display 22, while maintaining their relative positional relationship. Thus, it becomes intuitively easy to understand that the four diaphragm blades move in the upward direction as a result of an operation of inclining the operation stick 2325c in the far side. The same is the case when an operation is performed to incline the operation stick 2325c in the near-side direction, or the leftward direction, or the rightward direction, or some other arbitrary direction. That is, the operation stick 2325c enables intuitive operations with respect to the four diaphragm blades.

Moreover, for example, the operator operates the sticks 2321a, 2321b, 2321c, and 2321d as illustrated in FIG. 15. Then, according to every received operation, the acquisition function 241 moves the four diaphragm blades. For example, when the stick 2321a is operated, the acquisition function 241 moves the diaphragm blade 131a corresponding to the stick 2321a. Similarly, when the stick 2321b is operated, the acquisition function 241 moves the diaphragm blade 131b. Moreover, when the stick 2321c is operated, the acquisition function 241 moves the diaphragm blade 131c. Furthermore, when the stick 2321d is operated, the acquisition function 241 moves the diaphragm blade 131d.

That is, the operator can operate the sticks 2321a, 2321b, 2321c, and 2321d for independently operating the four diaphragm blades. As a result of the independent operations of the four diaphragm blades, the X-ray irradiation area that is formed by the four diaphragm blades has a change in the shape. Moreover, as a result of the change in the shape of the X-ray irradiation area, the shape of the first area R1, in which the real-time images are displayed, also changes as illustrated in a display example D3 illustrated in FIG. 15.

As described above, in the spot fluoroscopy mode, the position of the first area R1 can be adjusted using the operation stick 2325c, and the shape of the first area R1 can be adjusted using the sticks 2321a, 2321b, 2321c, and 2321d. For example, the operator adjusts the position and the shape of the first area R1 according to the position and the size of the region of interest in the subject P. As a result, while enabling real-time observation of the region of interest, the radiation exposure of the subject P can be reduced by keeping the X-ray irradiation area to the minimum possible size. Moreover, as a result of displaying the LIH, which is acquired in the past, in the second area R2 that is the surrounding area of the first area R1; it becomes possible to gain an understanding about the overall picture including the surrounding of the region of interest.

Figure 16:
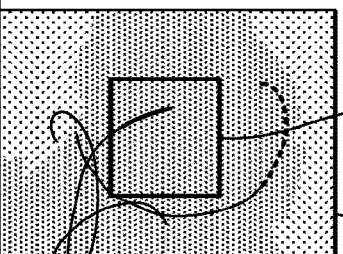

Explained below with reference to FIG. 16 is the case in which the spot ROI mode is set. FIG. 16 is a diagram illustrating an example of the fluoroscopy mode according to the first embodiment. In order to set the spot ROI mode, the operator operates the fluoroscopy mode switching button 2325b as illustrated in FIG. 16, for example.

In the case of performing fluoroscopy in the spot ROI mode, the acquisition function 241 causes retraction of the four diaphragm blades and uses a radiation dose reduction filter to acquire a plurality of X-ray images IM in chronological order. For example, when the spot ROI mode is set, the acquisition function 241 causes retraction of the four diaphragm blades and places the radiation dose reduction filter at the default position. The radiation dose reduction filter is formed in, for example, a torus shape and has a hole for irradiating the subject P with X-rays without causing attenuation. The operator presses the foot pedal and inputs an instruction for starting X-ray irradiation. In response to the instruction from the operator, the acquisition function 241 starts acquiring the X-ray images IM. The control function 242 sequentially displays the acquired X-ray images IM in the display 22.

As illustrated in a display D4 in FIG. 16, the X-ray image IM displayed in the display 22 has a first area R3 and a second area R4 that is the surrounding area of the first area R3. The first area R3 corresponds to the hole formed in the radiation dose reduction filter. That is, the X-ray image IM displayed in the first area R3 is acquired based on the X-rays that pass through the hole formed on the radiation dose reduction filter and fall onto the subject P without getting attenuated due to the radiation dose reduction filter. On the other hand, the X-ray image IM displayed in the second area R4 is acquired based on the X-rays that get attenuated because of transmitting through the radiation dose reduction filter.

Subsequently, the acquisition function 241 receives an operation with respect to the first area R3 from the operator. For example, as illustrated in FIG. 16, the operator operates the operation stick 2325c. In response to the operation of the operation stick 2325c, the acquisition function 241 makes the radiation dose reduction filter perform translational movement. As a result, as illustrated in a display example D5 in FIG. 16, the first area R3 that corresponds to the hole formed on the radiation dose reduction filter also moves.

For example, when an operation of inclining the operation stick 2325c in the far side is performed, the acquisition function 241 moves the first area R3 in the upward direction. That is, when an operation of inclining the operation stick 2325c in the far side is performed, the acquisition function 241 moves the radiation dose reduction filter in the upward direction of the X-ray image IM displayed in the display 22. Thus, it becomes intuitively easy to understand that an operation of inclining the operation stick 2325c in the far side results in the upward movement of the radiation dose reduction filter. The same is the case when an operation is performed to incline the operation stick 2325c in the near-side direction, or the leftward direction, or the rightward direction, or some other arbitrary direction. That is, the operation stick 2325c enables intuitive operations with respect to the radiation dose reduction filter.

As described above, in the spot ROI mode, the position of the first area R3 can be adjusted using the operation stick 2325c. For example, according to the position of the region of interest in the subject P, the operator adjusts the position of the first area R3. As a result, regarding the region of interest, the X-ray images IM of high image quality can be acquired using the X-rays that are bombarded onto the subject without any attenuation attributed to the radiation dose reduction filter.

Regarding the second area R4 that is the surrounding area of the first area R3, the X-ray images IM are acquired using the X-rays that are attenuated as a result transmitting through the radiation dose reduction filter, and thus the radiation exposure of the subject P can be reduced. Moreover, in the spot ROI mode, unlike in the spot fluoroscopy mode, real-time images can be displayed regarding the first area R3 as well as the second area R4.

As described above, according to the first embodiment, the first X-ray limiter 13 includes four diaphragm blades. On the diaphragm operation console 232, four operating units corresponding to the four diaphragm blades are placed at four positions. The four operating units are placed on the far side, the near side, the left side, and the right side when viewed by the operator of the diaphragm operation console 232. The far-side stick 2321a, the near-side stick 2321b, the left-side stick 2321c, and the right-side stick 2321d correspond to the upper diaphragm blade 131a, the lower diaphragm blade 131b, the left-side diaphragm blade 131c, and the right-side diaphragm blade 131d, respectively, with reference to the X-ray image IM displayed in the display 22. That is, the far-side stick 2321a, the near-side stick 2321b, the left-side stick 2321c, and the right-side stick 2321d receive operations for moving the upper diaphragm blade 131a, the lower diaphragm blade 131b, the left-side diaphragm blade 131c, and the right-side diaphragm blade 131d, respectively, with respect to the X-ray image IM displayed in the display 22. Thus, the X-ray diagnosis apparatus according to the first embodiment enables intuitive operations of the diaphragm blades and enables achieving enhancement in the operability related to the diaphragm blades.

For example, the sticks 2321a, 2321b, 2321c, and 2321d are placed in four directions of the far side, the near side, the left side, and the right side as illustrated in FIG. 13. Such an arrangement of the operating units is similar to the arrangement of the four diaphragm blades, thereby enabling the operator to intuitively understand which operating unit corresponds to which diaphragm blade.

For example, an operation of inclining the far-side stick 2321a in the far-side direction results in the movement of the upper diaphragm blade 131a in the upward direction of the X-ray image IM displayed in the display 22, and an operation of inclining the far-side stick 2321a in the near-side direction results in the movement of the upper diaphragm blade 131a in the downward direction of the X-ray image IM displayed in the display 22. Similarly, an operation of inclining the near-side stick 2321b in the far-side direction results in the movement of the lower diaphragm blade 131b in the upward direction of the X-ray image IM displayed in the display 22, and an operation of inclining the near-side stick 2321b in the near-side direction results in the movement of the lower diaphragm blade 131b in the downward direction of the X-ray image IM displayed in the display 22. Moreover, an operation of inclining the left-side stick 2321c in the leftward direction results in the movement of the left-side diaphragm blade 131c in the leftward direction of the X-ray image IM displayed in the display 22, and an operation of inclining the left-side stick 2321c in the rightward direction results in the movement of the left-side diaphragm blade 131c in the rightward direction of the X-ray image IM displayed in the display 22. Furthermore, an operation of inclining the right-side stick 2321d in the leftward direction results in the movement of the right-side diaphragm blade 131d in the leftward direction of the X-ray image IM displayed in the display 22, and an operation of inclining the right-side stick 2321d in the rightward direction results in the movement of the right-side diaphragm blade 131d in the rightward direction of the X-ray image IM displayed in the display 22. In this way, since the directions of operating the operating units match with the directions of movement of the corresponding diaphragm blades with respect to the X-ray image IM displayed in the display 22, the operator becomes able to intuitively understand the manner in which the operating units need to be operated in order to move the diaphragm blades in the desired directions.

As described above, according to the first embodiment, the diaphragm operation console 232 includes four sticks (the sticks 2321a, 2321b, 2321c, and 2321d) that receive inclination operations. That is, the diaphragm operation console 232 includes four physical operating units corresponding to four diaphragm blades. Hence, the operator of the diaphragm operation console 232 can recognize the operating units visually as well as tactually, and can operate the four operating units corresponding to the four diaphragm blades with more ease.

Moreover, as described above, according to the first embodiment, the four diaphragm blades can be individually moved. For example, the operator can operate any one of the sticks 2321a, 2321b, 2321c, and 2321d, and can independently operate each of the four diaphragm blades. Thus, the X-ray diagnosis apparatus according to the first embodiment enables achieving enhancement in the degree of freedom in operating the diaphragm blades.

Meanwhile, if the movement of two opposite diaphragm blades is to be coordinated while adjusting the diaphragm blades, then the operator can simultaneously operate the two corresponding operating units. For example, the operator can hold the far-side stick 2321a and the near-side stick 2321b at the same time with one hand, and can move the upper diaphragm blade 131a and the lower diaphragm blade 131b in a symmetrical manner and shorten the distance therebetween. In an identical manner, the operator can hold the left-side stick 2321c and the right-side stick 2321d at the same time with one hand, and can move the left-side diaphragm blade 131c and the right-side diaphragm blade 131d in a symmetrical manner and shorten the distance therebetween. For example, the far-side stick 2321a and the near-side stick 2321b are placed at such a distance from each other that they can be commonly and easily be held with one hand. As an example, the far-side stick 2321a and the near-side stick 2321b are placed at such a distance from each other that they can be held using the thumb and the index finger of the same hand. In an identical manner, the left-side stick 2321c and the right-side stick 2321d are placed at such a distance from each other than they can be commonly and easily be held with one hand.

As described above, according to the first embodiment, the first X-ray limiter 13 further includes the compensating filters 132a, 132b, and 132c. The diaphragm operation console 232 further includes the switching buttons 2322a and 2322b as switching units for switching between the diaphragm mode, which is meant for operating the four diaphragm blades, and the filter mode, which is meant for operating the three compensating filters.

There are similarities in operating the compensating filters and operating the diaphragm blades. For example, while operating the compensating filter 132a and while operating the diaphragm blade 131c, there is movement in the left-right direction with respect to the X-ray image IM displayed in the display 22. In that regard, in the diaphragm operation console 232, by switching between the diaphragm mode and the filter mode, the compensating filters as well as the diaphragm blades can be operated using the stick 2321c. Thus, as compared to the case in which the operating units for operating the diaphragm blades are provided separately from the operating units for operating the compensating filters, the X-ray diagnosis apparatus 1 enables achieving reduction in the number of operating units and downsizing the console. Moreover, as a result of reducing the number of operating units, the X-ray diagnosis apparatus 1 enables designing the operating units of a large size thereby making it easier to operate the console.

As described above, according to the first embodiment, when the filter mode is set; the sticks 2321c, 2321d, and 2321a receive operations with respect to the compensating filters 132a, 132b, and 132c, respectively. Thus, the X-ray diagnosis apparatus 1 according to the first embodiment enables intuitive operations with respect to the compensating filters and enables achieving enhancement in the operability related to the compensating filters.

For example, the sticks 2321c, 2321d, and 2321a are placed on the left side, the right side, and the far side, respectively, as illustrated in FIG. 13. Such an arrangement is similar to the arrangement of the compensating filter 132a representing the left-side filter, the compensating filter 132b representing the right-side filter, and the compensating filter 132c representing the upper-side filter. That enables the operator to intuitively understand which operating unit corresponds to which compensating filter.

In the case illustrated in FIG. 13, since there are three compensating filters, the stick 2321b from among the four operating units does not have a compensating filter corresponding thereto. Herein, since the sticks 2321c, 2321d, and 2321a corresponding to compensating filters have a different form than the stick 2321b not corresponding to any compensating filter, the operator can easily understand whether or not an operating unit correspond to a compensating filter.

Particularly, in the case illustrated in FIG. 13, as compared to the stick 2321b not corresponding to any compensating filter; the sticks 2321c, 2321d, and 2321a corresponding to compensating filters have a higher ratio of curved lines in the outer periphery and have an ideational association to the compensating filters that are rotatable. As a result, the operator can intuitively understand whether or not an operating unit corresponds to a compensating filter.

For example, an operation of inclining the stick 2321c in the leftward direction results in the movement of the compensating filter 132a in the leftward direction of the X-ray image IM displayed in the display 22, and an operation of inclining the stick 2321c in the rightward direction results in the movement of the compensating filter 132a in the rightward direction of the X-ray image IM displayed in the display 22. Moreover, an operation of inclining the stick 2321d in the leftward direction results in the movement of the compensating filter 132b in the leftward direction of the X-ray image IM displayed in the display 22, and an operation of inclining the stick 2321d in the rightward direction results in the movement of the compensating filter 132b in the rightward direction of the X-ray image IM displayed in the display 22. Furthermore, an operation of inclining the stick 2321a in the far-side direction results in the movement of the compensating filter 132c in the upward direction of the X-ray image IM displayed in the display 22, and an operation of inclining the stick 2321a in the near-side direction results in the movement of the compensating filter 132c in the downward direction of the X-ray image IM displayed in the display 22. In this way, since the directions of operating the operating units match with the directions of movement of the corresponding compensating filters with respect to the X-ray image IM displayed in the display 22, the operator becomes able to intuitively understand the manner in which the operating units need to be operated in order to move the compensating filters in the desired directions.

Moreover, for example, an operation of rotating the stick 2321c in the clockwise direction results in the rotation of the compensating filter 132a in the clockwise direction with respect to the X-ray image IM displayed in the display 22, and an operation of rotating the stick 2321c in the counterclockwise direction results in the rotation of the compensating filter 132a in the counterclockwise direction with respect to the X-ray image IM displayed in the display 22. Furthermore, an operation of rotating the stick 2321d in the clockwise direction results in the rotation of the compensating filter 132b in the clockwise direction with respect to the X-ray image IM displayed in the display 22, and an operation of rotating the stick 2321d in the counterclockwise direction results in the rotation of the compensating filter 132b in the counterclockwise direction with respect to the X-ray image IM displayed in the display 22. Moreover, an operation of rotating the stick 2321a in the clockwise direction results in the rotation of the compensating filter 132c in the clockwise direction with respect to the X-ray image IM displayed in the display 22, and an operation of rotating the stick 2321a in the counterclockwise direction results in the rotation of the compensating filter 132c in the counterclockwise direction with respect to the X-ray image IM displayed in the display 22. In this way, since the directions of rotation for operating the operating units match with the directions of rotation of the corresponding compensating filters with respect to the X-ray image IM displayed in the display 22, the operator becomes able to intuitively understand the manner in which the operating units need to be operated in order to adjust the orientation of the compensating filters in the desired directions.

As illustrated in FIG. 13, on the diaphragm operation console 232; the arm switching buttons 2324a and 2324b, the switching buttons 2322a and 2322b, and the sticks 2321a, 2321b, 2321c, and 2321d are arranged in that order starting from the far side. Such an arrangement is done according to the flow of operations performed by the operator. Hence, when a particular operation is over, the operator can intuitively understand the operation to be performed next.

For example, firstly, the operator operates the arm switching buttons 2324a and 2324b, which are disposed on the farthest side, and selects the arm to be operated. Then, the operator proceeds to the operation target on the nearer side and operates the switching buttons 2322a and 2322b, and selects whether to operate the diaphragm blades or to operate the compensating filters. Subsequently, the operator proceeds to the operation target on the still nearer side and operates the sticks 2321a, 2321b, 2321c, and 2321d, and performs operations with respect to the diaphragm blades or the compensating filters.

In the first embodiment described above, except for the case in which a plurality of operating units is simultaneously operated, the four diaphragm blades move individually because of the sticks 2321a, 2321b, 2321c, and 2321d. In contrast, in a second embodiment, the explanation is given for a case in which a coordinated-movement mode can be set for making a plurality of diaphragm blades perform coordinated movements.

The X-ray diagnosis apparatus 1 according to the second embodiment has an identical configuration to the X-ray diagnosis apparatus 1 illustrated in FIG. 1, with some differences in the operations performed by the acquisition function 241. Moreover, although the X-ray diagnosis apparatus 1 according to the second embodiment includes the diaphragm operation console 232 illustrated in FIG. 13, the diaphragm operation console 232 further includes a switch 2326 (not illustrated) for switching to the coordinated-movement mode. The switch 2326 represents an example of a coordination setting switch. Regarding the configuration identical to the configuration according to the first embodiment, the same reference numerals are used with reference to FIGS. 1 and 13, and the explanation is not repeated. In the second embodiment, the explanation is given for the case in which the first X-ray limiter 13 is set as the operation target and the diaphragm mode is set. Thus, in the second embodiment, the explanation is given for a case in which operations are received with respect to the diaphragm blades 131a, 131b, 131c, and 131d.

For example, the diaphragm operation console 232 includes, as the switch 2326 for switching to the coordinated-movement mode, a single button that enables switching between the coordinated-movement mode, in which a plurality of diaphragm blades is moved in coordination, and an individual operation mode, in which a diaphragm blade is individually moved. In that case, every time the concerned button is operated, the acquisition function 241 switches between the coordinated-movement mode and the individual operation mode.

Alternatively, for example, the diaphragm operation console 232 includes, as the switch 2326, a button corresponding to the coordinated-movement mode and a button corresponding to the individual operation mode. In that case, when the button corresponding to the coordinated-movement mode is operated, the acquisition function 241 sets the coordinated-movement mode; and, when the button corresponding to the individual operation mode is operated, the acquisition function 241 sets the individual operation mode.

Still alternatively, for example, the diaphragm operation console 232 includes, as the switch 2326, a stick for receiving an inclination operation. The stick can be inclinable only in predetermined directions or can be inclinable in arbitrary directions. According to the direction in which the operator inclines the stick, the acquisition function 241 switches between the coordinated-movement mode and the individual operation mode.

Still alternatively, for example, the diaphragm operation console 232 includes, as the switch 2326, an operating unit that receives sliding operations. The operating unit can be slidable in only predetermined directions or can be slidable in arbitrary directions. According to the direction in which operator slides the operating unit, the acquisition function 241 switches between the coordinated-movement mode and the individual operation mode.

Apart from that, the diaphragm operation console 232 can include arbitrary hardware as the switch 2326. For example, the diaphragm operation console 232 can include, as the switch 2326, a trackball, a wheel, a knob, or a grip that enables switching between the coordinated-movement mode and the individual operation mode according to the direction of rotation. Meanwhile, the switch 2326 can alternatively be installed on a different device other than the diaphragm operation console 232 illustrated in FIG. 13.

For example, when the individual operation mode is set; in response to the operations performed with respect to the sticks 2321a, 2321b, 2321c, and 2321d, the acquisition function 241 individually operates the diaphragm blades 131a, 131b, 131c, and 131d, respectively. On the other hand, when the coordinated-movement mode is set; in response to the operations performed with respect to the sticks 2321a, 2321b, 2321c, and 2321d, the acquisition function 241 moves a plurality of diaphragm blades in a coordinated manner from among the diaphragm blades 131a, 131b, 131c, and 131d.

For example, in the coordinated-movement mode, when either the far-side stick 2321a or the near-side stick 2321b is operated, the acquisition function 241 moves the diaphragm blades 131a and 131b in a symmetrical manner. As an example, in the coordinated-movement mode, when the stick 2321a is operated, the acquisition function 241 moves the diaphragm blade 131a according to the operation of the stick 2321a, as well as moves the diaphragm blade 131b in a symmetrical manner to the movement of the diaphragm blade 131a in the vertical direction of the X-ray image IM displayed in the display 22.

Alternatively, for example, in the coordinated-movement mode, when either the left-side stick 2321c or the right-side stick 2321d is operated, the acquisition function 241 moves the diaphragm blades 131c and 131d in a symmetrical manner. As an example, in the coordinated-movement mode, when the stick 2321c is operated, the acquisition function 241 moves the diaphragm blade 131c according to the operation of the stick 2321c, as well as moves the diaphragm blade 131d in a symmetrical manner to the movement of the diaphragm blade 131c in the horizontal direction of the X-ray image IM displayed in the display 22.

In the coordinated-movement mode, the operator can move a plurality of diaphragm blades by performing only a single operation. For example, in the coordinated-movement mode, by operating either the far-side stick 2321a or the near-side stick 2321b, it becomes possible to adjust the distance between the diaphragm blades 131a and 131b. On the other hand, in the individual operation mode, the operator can individually move the four diaphragm blades and thus can operate them with a higher degree of freedom.

Herein, the explanation is given about the case in which two opposite diaphragm blades are moved in a coordinated manner in the coordinated-movement mode. However, the embodiment is not limited to that case. Alternatively, for example, the acquisition function 241 can move two neighboring diaphragm blades in a coordinated manner. As an example, in the coordinated-movement mode, when the stick 2321a is operated in the far-side direction, the acquisition function 241 moves the diaphragm blade 131a in the upward direction of the X-ray image IM displayed in the display 22 as well as moves either the diaphragm blade 131c, which is neighboring to the diaphragm blade 131a, in the leftward direction of the X-ray image IM displayed in the display 22 or moves the diaphragm blade 131d, which is neighboring to the diaphragm blade 131a, in the rightward direction of the X-ray image IM displayed.

Alternatively, for example, the acquisition function 241 can move three diaphragm blades in a coordinated manner in the coordinated-movement mode. As an example, in the coordinated-movement mode, when the stick 2321a is operated in the far-side direction, the acquisition function 241 moves the diaphragm blade 131a in the upward direction of the X-ray image IM displayed in the display 22; moves the diaphragm blade 131c in the leftward direction of the X-ray image IM displayed in the display 22; and moves the diaphragm blade 131d in the rightward direction of the X-ray image IM displayed in the display 22. Still alternatively, the acquisition function 241 can move four diaphragm blades in a coordinated manner in the coordinated-movement mode.

Till now, the explanation was given about the first and second embodiments. However, it is also possible to implement various other forms other than the first and second embodiments.

In the first and second embodiments, of the four operating units (the sticks 2321a, 2321b, 2321c, and 2321d), the operating units corresponding to compensating filters are configured to be rotatable. However, the embodiments are not limited to that case.

For example, in the first and second embodiments, the stick 2321c that corresponds to the compensating filter 132a is inclinable in the rightward direction and the leftward direction, as well as is rotatable in the clockwise direction and the counterclockwise direction. However, instead of configuring the stick 2321c to be rotatable, it can be configured to be inclinable in the far-side direction and the near-side direction.

In the case of moving the compensating filter 132a with respect to the X-ray image IM displayed in the display 22, the operator inclines the stick 2321c in the leftward direction or the rightward direction. For example, an operation of inclining the stick 2321c in the leftward direction results in the movement of the compensating filter 132a in the leftward direction with respect to the X-ray image IM displayed in the display 22, and an operation of inclining the stick 2321c in the rightward direction results in the movement of the compensating filter 132a in the rightward direction with respect to the X-ray image IM displayed in the display 22. In this way, since the direction of operating the stick 2321c matches with the direction of movement of the compensating filter 132a, the operator becomes able to intuitively move the compensating filter 132a.

Alternatively, for example, in the case of rotating the compensating filter 132a with respect to the X-ray image IM displayed in the display 22, the operator inclines the stick 2321c in the far-side direction or the near-side direction. For example, an operation of inclining the stick 2321c in the far-side direction results in the rotation of the compensating filter 132a in the clockwise direction with respect to the X-ray image IM displayed in the display 22, and an operation of inclining the stick 2321c in the near-side direction results in the rotation of the compensating filter 132a in the counterclockwise direction with respect to the X-ray image IM displayed in the display 22.

Herein, considering the circumference of a circle passing through the sticks 2321a, 2321b, 2321c, and 2321d illustrated in FIG. 13, the operation of inclining the stick 2321c in the far-side direction is equivalent to a clockwise operation. In an identical manner, the operation of inclining the stick 2321c in the near-side direction is equivalent to a counterclockwise operation. In this way, since the direction of operating the stick 2321c is matched with the direction of rotation of the compensating filter 132a, the operator becomes able to intuitively rotate the compensating filter 132a.

Regarding the stick 2321d too, in an identical manner, instead of configuring it to be rotatable, it can be configured to be inclinable in the far-side direction and the near-side direction. For example, an operation of inclining the stick 2321d in the leftward direction results in the movement of the compensating filter 132b in the leftward direction with respect to the X-ray image IM displayed in the display 22, and an operation of inclining the stick 2321d in the rightward direction results in the movement of the compensating filter 132b in the rightward direction with respect to the X-ray image IM displayed in the display 22. Alternatively, an operation of operating the stick 2321d in the far-side direction results in the rotation of the compensating filter 132b in the counterclockwise direction with respect to the X-ray image IM displayed in the display 22, and an operation of operating the stick 2321d in the near-side direction results in the rotation of the compensating filter 132b rotates in the clockwise direction with respect to the X-ray image IM displayed in the display 22.

Regarding the stick 2321a too, in an identical manner, instead of configuring it to be rotatable, it can be configured to be inclinable in the leftward direction and the rightward direction. For example, an operation of inclining the stick 2321a in the far-side direction results in the movement of the compensating filter 132c in the upward direction with respect to the X-ray image IM displayed in the display 22, and an operation of inclining the stick 2321a in the near-side direction results in the movement of the compensating filter 132c in the downward direction with respect to the X-ray image IM displayed in the display 22. Moreover, an operation of inclining the stick 2321a in the leftward direction results in the rotation of the compensating filter 132c in the counterclockwise direction with respect to the X-ray image IM displayed in the display 22, and an operation of inclining the stick 2321a in the rightward direction results in the rotation of the compensating filter 132c in the clockwise direction with respect to the X-ray image IM displayed in the display 22.

Meanwhile, for example, it is possible to make appropriate changes in the hardware meant for implementing the operating units of the diaphragm operation console 232 illustrated in FIG. 13. For example, with reference to FIG. 13, the four sticks (the sticks 2321a, 2321b, 2321c, and 2321d) are illustrated as the four physical operating units corresponding to the four diaphragm blades. However, on the diaphragm operation console 232, the four sticks can be substituted with some other hardware.

For example, instead of including the four sticks, the diaphragm operation console 232 includes four operating units that receive sliding operations. As an example, the diaphragm operation console 232 includes an operating unit 2327a, which receives sliding operations, at the position of the stick 2321a illustrated in FIG. 13. In an identical manner, the diaphragm operation console 232 includes an operating unit 2327b at the position of the stick 2321b; includes an operating unit 2327c at the position of the stick 2321c; and includes an operating unit 2327d at the position of the stick 2321d. That is, when viewed from the side of the operator of the diaphragm operation console 232, the operating units 2327a, 2327b, 2327c, and 2327d are placed on the far side, the near side, the left side, and the right side, respectively.

For example, when the diaphragm mode is set, the operating units 2327a, 2327b, 2327c, and 2327d receive operations with respect to the diaphragm blades 131a, 131b, 131c, and 131d, respectively. Meanwhile, the operating units 2327a, 2327b, 2327c, and 2327d can be configured to be slidable only in predetermined directions or in arbitrary directions. For example, the operating units 2327a and 2327b are configured to be slidable in at least the far-side/near-side direction. Similarly, the operating units 2327c and 2327d are configured to be slidable in at least the leftward/rightward direction.

For example, when an operation of sliding the operating unit 2327a in the far-side direction is received, the acquisition function 241 moves the diaphragm blade 131a in the upward direction of the X-ray image IM displayed in the display 22. That is, an operation of sliding the operating unit 2327a in the far-side direction results in the movement of the diaphragm blade 131a in the upward direction of the X-ray image IM displayed in the display 22. Alternatively, for example, when an operation of sliding the operating unit 2327a in the near-side direction is received, the acquisition function 241 moves the diaphragm blade 131a in the downward direction of the X-ray image IM displayed in the display 22. That is, an operation of sliding the operating unit 2327a in the near-side direction results in the movement of the diaphragm blade 131a in the downward direction of the X-ray image IM displayed in the display 22.

The operating unit 2327a is placed on the far side of the operating units 2327b, 2327c, and 2327d, thereby making it intuitively easy to understand that the operating unit 2327a corresponds to the diaphragm blade 131a. Moreover, it is intuitively easy to understand that sliding the operating unit 2327a in the far-side direction results in the upward movement of the diaphragm blade 131a and that sliding the operating unit 2327a in the near-side direction results in the downward movement of the diaphragm blade 131a. That is, the operating unit 2327a enables intuitive operations with respect to the diaphragm blade 131a. In an identical manner, the operating units 2327b, 2327c, and 2327d enable intuitive operations with respect to the diaphragm blades 131b, 131c, and 131d, respectively.

Meanwhile, for example, when the filter mode is set, the operating units 2327c, 2327d, and 2327a receive operations with respect to the compensating filters 132a, 132b, and 132c, respectively. Moreover, for example, the operating units 2327c, 2327d, and 2327a are further configured to be rotatable in the clockwise direction and the counterclockwise direction. As an example, the operating unit 2327c is configured to be slidable in at least the leftward direction and the rightward direction, and is further configured to be rotatable with the direction substantially perpendicular to the far-side/near-side direction and the leftward/rightward direction serving as the rotation axis. For example, when performing an operation of rotating the operating unit 2327c, the operator holds and twists the operating unit 2327c and rotates it.

For example, when an operation of sliding the operating unit 2327c in the leftward direction is received, the acquisition function 241 moves the compensating filter 132a in the leftward direction of the X-ray image IM displayed in the display 22. That is, an operation of sliding the operating unit 2327c in the leftward direction results in the movement of the compensating filter 132a in the leftward direction of the X-ray image IM displayed in the display 22. Alternatively, for example, when an operation of sliding the operating unit 2327c in the rightward direction is received, the acquisition function 241 moves the compensating filter 132a in the rightward direction of the X-ray image IM displayed in the display 22. That is, an operation of sliding the operating unit 2327c in the rightward direction results in the movement of the compensating filter 132a in the rightward direction of the X-ray image IM displayed in the display 22.

Still alternatively, for example, when an operation of rotating the operating unit 2327c in the clockwise direction is received, the acquisition function 241 rotates the compensating filter 132a in the clockwise direction with respect to the X-ray image IM displayed in the display 22. That is, an operation of rotating the operating unit 2327c in the clockwise direction results in the rotation of the compensating filter 132a in the clockwise direction with respect to the X-ray image IM displayed in the display 22. Still alternatively, for example, when an operation of rotating the operating unit 2327c in the counterclockwise direction is received, the acquisition function 241 rotates the compensating filter 132a in the counterclockwise direction with respect to the X-ray image IM displayed in the display 22. That is, an operation of rotating the operating unit 2327c in the counterclockwise direction results in the rotation of the compensating filter 132a in the counterclockwise direction with respect to the X-ray image IM displayed in the display 22.

The compensating filter 132a is a left-side filter that is inserted from the left side with respect to the X-ray image IM displayed in the display 22. Thus, it is intuitively easy to understand that the operating unit 2327c, which is placed on the left side of the operating units 2327a, 2327b, and 2327d, corresponds to the compensating filter 132a representing the left-side filter. Moreover, it is also intuitively easy to understand that sliding the operating unit 2327c in the leftward direction results in the leftward movement of the compensating filter 132a, and that sliding the operating unit 2327c in the rightward direction results in the rightward movement of the compensating filter 132a. Furthermore, it is also intuitively easy to understand that rotating the operating unit 2327c in the clockwise direction results in the clockwise rotation of the compensating filter 132a, and that rotating the operating unit 2327c in the counterclockwise direction results in the counterclockwise rotation of the compensating filter 132a. That is, the operating unit 2327c enables intuitive operations with respect to the compensating filter 132a. In an identical manner, the operating units 2327d and 2327a enable intuitive operations with respect to the compensating filters 132b and 132c, respectively.

Meanwhile, in an identical manner to the cases of the sticks 2321c and 2321d, instead of configuring the operating units 2327c and 2327d to be rotatable, they can be configured to be further slidable in the far-side direction and the near-side direction. In that case, an operation of sliding the operating unit 2327c in the far-side direction results in the rotation of the compensating filter 132a in the clockwise direction with respect to the X-ray image IM displayed in the display 22, and an operation of sliding the operating unit 2327c in the near-side direction results in the rotation of the compensating filter 132a in the counterclockwise direction with respect to the X-ray image IM displayed in the display 22. Moreover, an operation of sliding the operating unit 2327d in the far-side direction results in the rotation of the compensating filter 132b in the counterclockwise direction with respect to the X-ray image IM displayed in the display 22, and an operation of sliding the operating unit 2327d in the near-side direction results in the rotation of the compensating filter 132b in the clockwise direction with respect to the X-ray image IM displayed in the display 22.

In an identical manner to the case of the stick 2321a, instead of configuring the operating unit 2327a to be rotatable, it can be configured to be slidable in the leftward direction and the rightward direction. In that case, an operation of sliding the operating unit 2327a in the leftward direction results in the rotation of the compensating filter 132c in the counterclockwise direction with respect to the X-ray image IM displayed in the display 22, and an operation of sliding the operating unit 2327a in the rightward direction results in the rotation of the compensating filter 132c in the clockwise direction with respect to the X-ray image IM displayed in the display 22.

As another example, instead of including four sticks, the diaphragm operation console 232 includes four wheel-shaped operating units. As an example, the diaphragm operation console 232 includes, at the position of the stick 2321a illustrated in FIG. 13, a wheel-shaped operating unit 2328a that is rotatable with the direction substantially parallel to the leftward/rightward direction serving as the rotation axis. Similarly, the diaphragm operation console 232 includes, at the position of the stick 2321b, a wheel-shaped operating unit 2328b that is rotatable with the direction substantially parallel to the leftward/rightward direction serving as the rotation axis. Moreover, the diaphragm operation console 232 includes, at the position of the stick 2321c, a wheel-shaped operating unit 2328c that is rotatable with the direction substantially parallel to the far-side/near-side direction serving as the rotation axis. Furthermore, the diaphragm operation console 232 includes, at the position of the stick 2321d, a wheel-shaped operating unit 2328d that is rotatable with the direction substantially parallel to the far-side/near-side direction serving as the rotation axis. That is, when viewed from the side of the operator of the diaphragm operation console 232, the operating units 2328a, 2328b, 2328c, and 2328d are placed on the far side, the near side, the left side, and the right side, respectively. For example, when the diaphragm mode is set, the operating units 2328a, 2328b, 2328c, and 2328d receive operations with respect to the diaphragm blades 131a, 131b, 131c, and 131d, respectively.

For example, while touching the operating unit 2328a with a hand, the operator moves that hand in the far-side direction. As a result, the operating unit 2328a rotates with the direction substantially parallel to the leftward/rightward direction as the rotation axis. More particularly, the operating unit 2328a rotates in the clockwise direction when viewed from the rightward direction. In this way, when an operation of rotating the operating unit 2328a in the far-side direction is received, the acquisition function 241 moves the diaphragm blade in the upward direction of the X-ray image IM displayed in the display 22. That is, an operation of rotating the operating unit 2328a in the far-side direction results in the movement of the diaphragm blade 131a in the upward direction of the X-ray image IM displayed in the display 22. Alternatively, when an operation of rotating the operating unit 2328a in the near-side direction is received, the acquisition function 241 moves the diaphragm blade 131a in the downward direction. That is, an operation of rotating the operating unit 2328a in the near-side direction results in the movement of the diaphragm blade 131a in the downward direction of the X-ray image IM displayed in the display 22.

Herein, the operating unit 2328a is placed on the far side of the operating units 2328b, 2328c, and 2328d. Thus, it is intuitively easy to understand that the operating unit 2328a corresponds to the diaphragm blade 131a. Moreover, it is also intuitively easy to understand that rotating the operating unit 2328a in the far-side direction results in the upward movement of the diaphragm blade, and that rotating the operating unit 2328a in the near-side direction results in the downward movement of the diaphragm blade. That is, the operating unit 2328a enables intuitive operations with respect to the diaphragm blade 131a. In an identical manner, the operating units 2328b, 2328c, and 2328d enable intuitive operations with respect to the diaphragm blades 131b, 131c, and 131d.

Meanwhile, for example, when the filter mode is set, the operating units 2328c, 2328d, and 2328a receive operations with respect to the compensating filters 132a, 132b, and 132c, respectively. For example, the operating units 2328c, 2328d, and 2328a are further configured to be rotatable in the clockwise direction and the counterclockwise direction.

For example, the operating unit 2328c is rotatable with the direction substantially parallel to the far-side/near-side direction serving as the rotation axis, and is further configured to be rotatable with the direction substantially perpendicular to the far-side/near-side direction and the leftward/rightward direction serving as the rotation axis.

As an example, the operating unit 2328c is a circular wheel-shaped operating unit when viewed from the far-side direction or the near-side direction. Moreover, the operating unit 2328c is configured to be rotatable with the axis that is substantially parallel to the far-side/near-side direction and that passes through the operating unit 2328c serving as the rotation axis. For example, while touching the operating unit 2328c with a hand, the operator moves that hand in the left-right direction, and rotates the operating unit 2328c with the direction substantially parallel to the far-side/near-side direction serving as the rotation axis.

Meanwhile, when viewed from the direction substantially perpendicular to the far-side/near-side direction and the leftward/rightward direction (for example, when viewed while facing the diaphragm operation console 232), for example, the operating unit 2328c has an elliptical shape or a quadrangular shape, or has the shape of a figure with the outer periphery made of two straight lines and two curved lines, or has the shape of a figure with the outer periphery made of four straight lines and four curved lines that join the straight lines. The operating unit 2328c either can have the far-side/near-side direction as the long direction or can have the leftward/rightward direction as the long direction. Moreover, the operating unit 2328c is configured to be rotatable with the axis that is substantially perpendicular to the far-side/near-side direction and that passes through the center of the operating unit 2328c serving as the rotation axis. The operator holds and twists the operating unit 2328c and rotates it with the direction substantially perpendicular to the far-side/near-side direction and the leftward/rightward direction serving as the rotation axis.

In order to move the compensating filter 132a, the operator rotates the operating unit 2328c with the direction substantially parallel to the far-side/near-side direction serving as the rotation axis. For example, while touching the operating unit 2328c with a hand, the operator moves that hand in the leftward direction. As a result, the operating unit 2328c rotates with the direction substantially parallel to the far-side/near-side direction serving as the rotation axis. More particularly, the operating unit 2328a rotates in the clockwise direction when viewed from the near-side direction. In this way, when an operation of moving the operating unit 2328c in the leftward direction is received, the acquisition function moves the compensating filter 132a in the leftward direction of the X-ray image IM displayed in the display 22. That is, an operation of moving the operating unit 2328c in the leftward direction results in the movement of the compensating filter 132a in the leftward direction of the X-ray image IM displayed in the display 22. Alternatively, when an operation of moving the operating unit 2328c in the rightward direction is received, the acquisition function moves the compensating filter 132a in the rightward direction of the X-ray image IM displayed in the display 22. That is, an operation of moving the operating unit 2328c in the rightward direction results in the movement of the compensating filter 132a in the rightward direction of the X-ray image IM displayed in the display 22.

Meanwhile, for example, in order to rotate the compensating filter 132a, the operator rotates the operating unit

2328c with the direction substantially perpendicular to the far-side/near-side direction and the leftward/rightward direction. For example, the operator holds and twists the operating unit 2328c and rotates in the clockwise direction or the counterclockwise direction.

When an operation of rotating the operating unit 2328c in the clockwise direction is received, the acquisition function 241 rotates the compensating filter 132a in the clockwise direction with respect to the X-ray image IM displayed in the display 22. That is, an operation of rotating the operating unit 2328c in the clockwise direction results in the rotation of the compensating filter 132a in the clockwise direction with respect to the X-ray image IM displayed in the display 22. Alternatively, when an operation of rotating the operating unit 2328c in the counterclockwise direction is received, the acquisition function 241 rotates the compensating filter 132a in the counterclockwise direction with respect to the X-ray image IM displayed in the display 22. That is, an operation of rotating the operating unit 2328c in the counterclockwise direction results in the rotation of the compensating filter 132a in the counterclockwise direction with respect to the X-ray image IM displayed in the display 22.

The compensating filter 132a is a left-side filter that is inserted from the left side with respect to the X-ray image IM displayed in the display 22. Thus, it is intuitively easy to understand that the operating unit 2328c, which is placed on the left side of the operating units 2328b and 2328d, corresponds to the compensating filter 132a representing the left-side filter. Moreover, it is also intuitively easy to understand that an operation of moving the operating unit 2328c in the leftward direction results in the leftward movement of the compensating filter 132a, and that an operation of moving the operating unit 2328c in the rightward direction results in the rightward movement of the compensating filter 132a. Furthermore, it is also intuitively easy to understand that an operation of rotating the operating unit 2328c in the clockwise direction results in the clockwise rotation of the compensating filter 132a, and that an operation of rotating the operating unit 2328c in the counterclockwise direction results in the counterclockwise rotation of the compensating filter 132a. That is, the operating unit 2328c enables intuitive operations with respect to the compensating filter 132a. In an identical manner, the operating units 2328d and 2328a enable intuitive operations with respect to the compensating filters 132b and 132c, respectively.

In an identical manner to the cases of the sticks 2321c and 2321d, instead of configuring the operating units 2328c and 2328d with the direction substantially perpendicular to the far-side/near-side direction serving as the rotation axis, they can be configured to be further inclinable in the far-side direction and the near-side direction. In that case, an operation of moving the operating unit 2328c in the far-side direction results in the rotation of the compensating filter 132a in the clockwise direction with respect to the X-ray image IM displayed in the display 22, and an operation of moving the operating unit 2328c in the near-side direction results in the rotation of the compensating filter 132a in the counterclockwise direction with respect to the X-ray image IM displayed in the display 22. Alternatively, an operation of moving the operating unit 2328d in the far-side direction results in the rotation of the compensating filter 132b in the counterclockwise direction with respect to the X-ray image IM displayed in the display 22, and an operation of moving the operating unit 2328d in the near-side direction results in the rotation of the compensating filter 132b in the clockwise direction with respect to the X-ray image IM displayed in the display 22.

In an identical manner to the case of the stick 2321a, instead of configuring the operating unit 2328a to be rotatable with the direction substantially perpendicular to the far-side/near-side direction and the leftward/rightward direction serving as the rotation axis, the operating unit 2328a can be configured to be further inclinable in the leftward direction and the rightward direction. In that case, an operation of moving the operating unit 2328a in the leftward direction results in the rotation of the compensating filter 132c in the counterclockwise direction with respect to the X-ray image IM displayed in the display 22, and an operation of moving the operating unit 2328a in the rightward direction results in the rotation of the compensating filter 132c in the clockwise direction with respect to the X-ray image IM displayed in the display 22.

With reference to FIG. 13, the switching buttons 2322a and 2322b are used as the switching units for switching between the diaphragm mode, which is meant for operating the diaphragm blades, and the filter mode, which is meant for operating the compensating filters. However, instead of including the two buttons, the diaphragm operation console 232 can include some other hardware. For example, instead of including the switching buttons 2322a and 2322b, the diaphragm operation console 232 can include only a single button for switching between the diaphragm mode and the filter mode. In that case, every time the button is operated, the acquisition function 241 switches between the diaphragm mode and the filter mode.

Still alternatively, for example, instead of including the switching buttons 2322a and 2322b, the diaphragm operation console 232 can include a stick for receiving inclination operations. In that case, according to the direction in which the stick is inclined by the operator, the acquisition function 241 switches between the diaphragm mode and the filter mode. Still alternatively, for example, instead of including the switching buttons 2322a and 2322b, the diaphragm operation console 232 can include an operating unit for receiving sliding operations. In that case, according to the direction in which the operating unit is slid by the operator, the acquisition function 241 switches between the diaphragm mode and filter mode.

Apart from that, instead of including the switching buttons 2322a and 2322b, the diaphragm operation console 232 can include arbitrary hardware. For example, instead of including the switching buttons 2322a and 2322b, the diaphragm operation console 232 can include a trackball, a wheel, a knob, or a grip that, according to the direction of rotation thereof, switches between the diaphragm mode and the filter mode.

With reference to FIG. 13, the open button 2323 is used as the operating unit for causing retraction of a plurality of diaphragm blades all at once. However, instead of including the open button 2323, the diaphragm operation console 232 can include some other hardware. For example, instead of including the open button 2323, the diaphragm operation console 232 can include a stick for receiving inclination operations. In that case, for example, with the inclination of the stick in a predetermined trigger serving as the trigger, the acquisition function 241 causes retraction of a plurality of diaphragm blades all at once. Alternatively, for example, instead of including the open button 2323, the diaphragm operation console 232 can include an operating unit for receiving sliding operations. In that case, for example, with the sliding of the operating unit in a predetermined direction serving as the trigger, the acquisition function 241 causes retraction of a plurality of diaphragm blades all at once.

Apart from that, instead of including the open button 2323, the diaphragm operation console 232 can include arbitrary hardware.

With reference to FIG. 13, the arm switching buttons 2324a and 2324b are used as the switches for switching between receiving operations with respect to the first X-ray limiter 13 and receiving operations with respect to the second X-ray limiter 17. However, instead of including those two buttons, the diaphragm operation console 232 can include some other hardware. For example, instead of including the arm switching buttons 2324a and 2324b, the diaphragm operation console 232 can include only a single button for switching between the target arms for operation. In that case, every time the button is operated, the acquisition function 241 switches between receiving operations with respect to the first X-ray limiter 13 and receiving operations with respect to the second X-ray limiter 17.

Alternatively, for example, instead of including the arm switching buttons 2324a and 2324b, the diaphragm operation console 232 can include a stick for receiving inclination operations. In that case, according to the direction in which the stick is inclined by the operator, the acquisition function 241 switches between receiving operations with respect to the first X-ray limiter 13 and receiving operations with respect to the second X-ray limiter 17. Still alternatively, for example, instead of including the arm switching buttons 2324a and 2324b, the diaphragm operation console 232 can include an operating unit for receiving sliding operations. In that case, according to the direction in which the operating unit is slid by the operator, the acquisition function 241 switches between receiving operations with respect to the first X-ray limiter 13 and receiving operations with respect to the second X-ray limiter 17.

Apart from that, instead of including the arm switching buttons 2324a and 2324b, the diaphragm operation console 232 can include arbitrary hardware. For example, instead of including the arm switching buttons 2324a and 2324b, the diaphragm operation console 232 can include a trackball, a wheel, a knob, or a grip that, according to the direction of rotation thereof, switches between the target arms for operation.

With reference to FIG. 13, the fluoroscopy mode switching buttons 2325a and 2325b are used as the switches for switching between the fluoroscopy modes. However, instead of including those two buttons, the diaphragm operation console 232 can include some other hardware. For example, instead of including the fluoroscopy mode switching buttons 2325a and 2325b, the diaphragm operation console 232 can include only a single button for switching between the fluoroscopy modes. In that case, every time the button is operated, the acquisition function 241 switches the fluoroscopy mode between, for example, the spot fluoroscopy mode and the spot ROI mode.

Alternatively, for example, instead of including the fluoroscopy mode switching buttons 2325a and 2325b, the diaphragm operation console 232 can include a stick for receiving inclination operations. In that case, according to the direction in which the stick is inclined by the operator, the acquisition function 241 switches between the fluoroscopy modes. Still alternatively, for example, instead of including the fluoroscopy mode switching buttons 2325a and 2325b, the diaphragm operation console 232 can include an operating unit for receiving sliding operations. In that case, according to the direction in which the operating unit is slid by the operator, the acquisition function 241 switches between the fluoroscopy modes.

Apart from that, instead of including the fluoroscopy mode switching buttons 2325a and 2325b, the diaphragm operation console 232 can include arbitrary hardware. For example, instead of including the fluoroscopy mode switching buttons 2325a and 2325b, the diaphragm operation console 232 can include a trackball, a wheel, a knob, or a grip that, according to the direction of rotation thereof, switches between the fluoroscopy modes.

With reference to FIG. 13, the operation stick 2325c is used as the operating unit for moving the position of the X-ray irradiation area, which is formed by the four diaphragm blades, with respect to the subject P while maintaining the shape of the X-ray irradiation area. However, instead of including the operation stick 2325c, the diaphragm operation console 232 can include some other hardware.

For example, instead of including the operation stick 2325c, the diaphragm operation console 232 can include a plurality of buttons. As an example, instead of including the operation stick 2325c, the diaphragm operation console 232 includes four buttons that are placed on the far side, the near side, the left side, and the right side when viewed from the side of the operator of the diaphragm operation console 232. In that case, according to the operated button, the acquisition function 241 moves the position of the X-ray irradiation area with respect to the subject P. For example, when the far-side button is operated, the acquisition function 241 moves the X-ray irradiation area in the upward direction of the X-ray IM displayed in the display 22. Alternatively, for example, when the near-side button is operated, the acquisition function 241 moves the X-ray irradiation area in the downward direction of the X-ray IM displayed in the display 22. Still alternatively, for example, when the left-side button is operated, the acquisition function 241 moves the X-ray irradiation area in the leftward direction of the X-ray IM displayed in the display 22. Still alternatively, for example, when the right-side button is operated, the acquisition function 241 moves the X-ray irradiation area in the rightward direction of the X-ray IM displayed in the display 22.

Meanwhile, for example, instead of including the operation stick 2325c, the diaphragm operation console 232 can include an operating unit for receiving sliding operations. In that case, according to the direction in which the operating unit is slid by the operator, the acquisition function 241 moves the position of the X-ray irradiation area with respect to the subject P. Alternatively, for example, instead of including the operation stick 2325c, the diaphragm operation console 232 can include a trackball. In that case, according to the direction in which the trackball is rotated by the operator, the acquisition function 241 moves the position of the X-ray irradiation area with respect to the subject P. Apart from that, instead of including the operation stick 2325c, the diaphragm operation console 232 can include arbitrary hardware.

In the embodiments described above, the first X-ray limiter 13 includes the compensating filter 132a representing the left-side filter, the compensating filter 132b representing the right-side filter, and the compensating filter 132c representing the upper-side filter. However, the embodiments are not limited to that case. For example, instead of including the compensating filter 132a representing the left-side filter, the first X-ray limiter 13 can include a compensating filter 132d representing the lower-side filter. Thus, when the filter mode is set, for example, the sticks 2321d, 2321a, and 2321b receive operations with respect to the compensating filters 132b, 132c, and 132d, respectively.

In an identical manner, instead of including the compensating filter 132b representing the right-side filter, the first X-ray limiter 13 can include the compensating filter 132d representing the lower-side filter. Moreover, in an identical manner, instead of including the compensating filter 132c representing the upper-side filter, the first X-ray limiter 13 can include the compensating filter 132d representing the lower-side filter.

In the embodiments described above, the first X-ray limiter 13 includes three compensating filters. However, the embodiments are not limited to that case. Alternatively, for example, the first X-ray limiter 13 can include four compensating filters, namely, the compensating filter 132a representing the left-side filter, the compensating filter 132b representing the right-side filter, the compensating filter 132c representing the upper-side filter, and the compensating filter 132d representing the lower-side filter. When the filter mode is set, for example, the sticks 2321c, 2321d, 2321a, and 2321b receive operations with respect to the compensating filters 132a, 132b, 132c, and 132d, respectively. Still alternatively, for example, the first X-ray limiter 13 can include only two compensating filters or only a single compensating filter.

In the embodiments described above, the first X-ray limiter 13 includes at least a single compensating filter. However, the embodiments are not limited to that case. That is, the first X-ray limiter 13 can be configured not to include any compensating filter.

When the first X-ray limiter 13 does not include any compensating filter, the diaphragm operation console 232 can be configured not to include switching units such as the switching buttons 2322a and 2322b for switching between the diaphragm mode and the filter mode. For example, when the first X-ray limiter 13 does not include any compensating filter, the diaphragm mode is set on a continuous basis and the sticks 2321a, 2321b, 2321c, and 2321d receive operations with respect to the four diaphragm blades.

Also in the case in which the first X-ray limiter 13 includes compensating filters, the diaphragm operation console 232 can be configured not to include a switching unit for switching between the diaphragm mode and the filter mode. For example, the sticks 2321a, 2321b, 2321c, and 2321d receive operations with respect to the four diaphragm blades, and the operations with respect to compensating filters can be received by a separate input interface other than the diaphragm operation console 232.

In the embodiments described above, the first X-ray limiter 13 includes four diaphragm blades. However, the embodiments are not limited to that case. Alternatively, for example, the first X-ray limiter 13 can be configured to include only three diaphragm blades, or only two diaphragm blades, or only a single diaphragm blade.

As an example, the first X-ray limiter 13 includes, as the diaphragm blade, only the diaphragm blade 131a on the upper side of the X-ray image IM displayed in the display 22; and includes, as the compensating filter, only the compensating filter 132c representing the upper-side filter. In that case, for example, from among the four operating units (the sticks 2321a, 2321b, 2321c, and 2321d) illustrated in FIG. 13, the first X-ray limiter 13 includes at least the far-side stick 2321a.

When the diaphragm mode is set, the stick 2321a receives operations with respect to the diaphragm blade 131a; and, when the filter mode is set, the stick 2321a receives operations with respect to the compensating filter 132c. In other words, in the diaphragm mode, operations with respect to the diaphragm blade 131a are assigned to the stick 2321a. In the filter mode, operations with respect to the compensating filter 132c are assigned to the stick 2321a.

As another example, the first X-ray limiter 13 includes, as the diaphragm blade, only the diaphragm blade 131a placed on the upper side of the X-ray image IM displayed in the display 22; and includes, as the compensating filter, only the compensating filter 132a representing the left-side filter. In that case, for example, from among the four operating units (the sticks 2321a, 2321b, 2321c, and 2321d) illustrated in FIG. 13, the first X-ray limiter 13 includes the far-side stick 2321a and the left-side stick 2321c.

When the diaphragm mode is set, the stick 2321a receives operations with respect to the diaphragm blade 131a; and, when the filter mode is set, the stick 2321c receives operations with respect to the compensating filter 132a. In other words, in the diaphragm mode, operations with respect to the diaphragm blade 131a are assigned to the sticks 2321a and 2321c. In the filter mode, operations with respect to the compensating filter 132a are assigned to the sticks 2321a and 2321c.

In an identical manner, regarding the diaphragm blades and the compensating filters included in the first X-ray limiter 13, changes can be made in an arbitrary manner. That is, the first X-ray limiter 13 includes at least a single diaphragm blade and at least a single compensating filter. Moreover, according to the diaphragm blades and the compensating filters included in the first X-ray limiter 13, the diaphragm operation console 232 includes at least a single operating unit meant for operating the at least single diaphragm blade and the at least single compensating filter. Furthermore, the diaphragm operation console 232 includes switching units, such as the switching buttons 2322a and 2322b illustrated in FIG. 13, that are meant for switching between the mode in which operations with respect to the at least single diaphragm blade are assigned to the at least single physical operating unit and the mode in which operations with respect to the at least single compensating filter are assigned to the at least single physical operating unit.

In the embodiments described above, the first X-ray limiter 13 includes at least a single diaphragm blade. However, the embodiments are not limited to that case. That is, the first X-ray limiter 13 can be configured not to include any diaphragm blade. In that case, for example, from among the four operating units (the sticks 2321a, 2321b, 2321c, and 2321d) illustrated in FIG. 13, the diaphragm operation console 232 includes at least a single operating unit for receiving operations with respect to the compensating filters included in the first X-ray limiter 13.

For example, when the first X-ray limiter 13 does not include any diaphragm blade and includes, as the compensating filter, only the compensating filter 132a representing the left-side filter, the diaphragm operation console 232 includes, for example, at least the left-side stick 2321c. Herein, for example, the stick 2321c is configured to be able to receive operations for movement in the leftward direction, operations for movement in the rightward directions, operations for rotation in the clockwise direction, and operations for rotation in the counterclockwise direction. Thus, an operation of moving the stick 2321c in the leftward direction results in the translational movement of the compensating filter 132a in the leftward direction of the X-ray image IM displayed in the display 22; an operation of moving the stick 2321c in the rightward direction results in the translational movement of the compensating filter 132a in the rightward direction of the X-ray image IM displayed in the display 22; an operation of rotating the stick 2321c in the clockwise direction results in the rotation of the compensating filter 132a in the clockwise direction with respect to the X-ray image IM displayed in the display 22; and an operation of rotating the stick 2321c in the counterclockwise direction results in the rotation of the compensating filter 132a in the counterclockwise direction with respect to the X-ray image IM displayed in the display 22.

When the first X-ray limiter 13 further includes the compensating filter 132b representing the right-side filter, the diaphragm operation console 232 at least includes the left-side stick 2321c and the right-side stick 2321d. That is, the first X-ray limiter 13 includes the compensating filter 132a that is inserted from the left side with respect to the X-ray image IM displayed in the display 22; and includes the compensating filter 132b that is inserted from the right side with respect to the X-ray image IM displayed in the display 22. Moreover, the sticks 2321c and 2321d are placed on the diaphragm operation console 232. When viewed from the side of the operator of the diaphragm operation console 232, the sticks 2321c and 2321d are placed on the left side and the right side, respectively. The stick 2321c receives operations with respect to the compensating filter 132a. The stick 2321d receives operations with respect to the compensating filter 132b.

For example, the stick 2321d is configured to be able to receive operations for movement in the leftward direction, operations for movement in the rightward directions, operations for rotation in the clockwise direction, and operations for rotation in the counterclockwise direction. Thus, an operation of moving the stick 2321d in the leftward direction results in the translational movement of the compensating filter 132b in the leftward direction of the X-ray image IM displayed in the display 22; an operation of moving the stick 2321d in the rightward direction results in the translational movement of the compensating filter 132b in the rightward direction of the X-ray image IM displayed in the display 22; an operation of rotating the stick 2321d in the clockwise direction results in the rotation of the compensating filter 132b in the clockwise direction with respect to the X-ray image IM displayed in the display 22; and an operation of rotating the stick 2321d in the counterclockwise direction results in the rotation of the compensating filter 132b in the counterclockwise direction with respect to the X-ray image IM displayed in the display 22.

When the first X-ray limiter 13 further includes the compensating filter 132c representing the upper-side filter, the diaphragm operation console 232 at least includes the left-side stick 2321c, the right-side stick 2321d, and the far-side stick 2321a. That is, the first X-ray limiter 13 further includes the compensating filter 132c that is inserted from the right side with respect to the X-ray image IM displayed in the display 22. Moreover, the stick 2321a is further placed on the diaphragm operation console 232. Thus, when viewed from the side of the operator of the diaphragm operation console 232, the stick 2321a is placed on the far side of the stick 2321c and the stick 2321d. The stick 2321a receives operations with respect to the compensating filter 132c.

The stick 2321a is configured to be able to receive operations for movement in the far-side direction, operations for movement in the near-side directions, operations for rotation in the clockwise direction, and operations for rotation in the counterclockwise direction. Thus, an operation of moving the stick 2321a in the far-side direction results in the translational movement of the compensating filter 132c in the upward direction of the X-ray image IM displayed in the display 22; an operation of moving the stick 2321a in the near-side direction results in the translational movement of the compensating filter 132c in the downward direction of the X-ray image IM displayed in the display 22; an operation of rotating the stick 2321a in the clockwise direction results in the rotation of the compensating filter 132c in the clockwise direction with respect to the X-ray image IM displayed in the display 22; and an operation of rotating the stick 2321a in the counterclockwise direction results in the rotation of the compensating filter 132c in the counterclockwise direction with respect to the X-ray image IM displayed in the display 22.

Herein, the explanation is given about the following cases: the case in which the first X-ray limiter 13 includes only the compensating filter 132a; the case in which the first X-ray limiter 13 includes the compensating filters 132a and 132b; and the case in which the first X-ray limiter 13 includes the compensating filters 132a, 132b, and 132c. However, the number of compensating filters included in the first X-ray limiter 13 can be appropriately changed. For example, the first X-ray limiter 13 can include only the compensating filter 132b representing the right-side filter, or can include only the compensating filter 132c representing the upper-side filter, or can include only the compensating filter 132d representing the lower-side filter. Alternatively, for example, the first X-ray limiter 13 can include the compensating filters 132a and 132c, or can include the compensating filters 132a and 132d, or can include the compensating filters 132b and 132c, or can include the compensating filters 132b and 132d, or can include the compensating filters 132c and 132d. Still alternatively, for example, the first X-ray limiter 13 can include the compensating filters 132a, 132b, and 132d; or can include the compensating filters 132a, 132c, and 132d; or can include the compensating filters 132b, 132c, and 132d. Still alternatively, for example, the first X-ray limiter 13 can include the compensating filters 132a, 132b, 132c, and 132d.

In this way, the first X-ray limiter 13 includes at least a single compensating filter. Moreover, the diaphragm operation console 232 includes at least a single operating unit corresponding to the compensating filter included in the first X-ray limiter 13, and the operating unit receives operations with respect to the compensating filter included in the first X-ray limiter 13. For example, the at least single operating unit included in the diaphragm operation console 232 receives operations in at least one of the far-side direction, the near-side direction, the leftward direction, and the rightward direction. Thus, an operation of moving the at least single operating unit in at least one of the far-side direction, the near-side direction, the leftward direction, and the rightward direction results in the translational movement of the at least single compensating filter that is included in the first X-ray limiter 13. Moreover, the at least single operating unit included in the diaphragm operation console 232 receives operations for rotating in at least the clockwise direction or the counterclockwise direction. Thus, an operation of rotating the at least single operating unit in at least the clockwise direction or the counterclockwise direction results in the rotation of the at least single compensating filter that is included in first X-ray limiter 13.

When the first X-ray limiter 13 does not include any diaphragm blade, the diaphragm operation console 232 can be configured not to include the switching units, such as the switching buttons 2322a and 2322b, for switching between the diaphragm mode and the filter mode. For example, when the first X-ray limiter 13 does not include any diaphragm blade, the filter mode can be set on a continuous basis. Moreover, also when the first X-ray limiter 13 includes diaphragm blades, the diaphragm operation console can be configured not to include the switching units for switching between the diaphragm mode and the filter mode. For example, the at least single operating unit included in the diaphragm operation console 232 can receive operations with respect to the compensating filter included in the first X-ray limiter 13, and the operations with respect to diaphragm blades can be received by a separate input interface other than the diaphragm operation console 232.

In the embodiments described above, the operations with respect to the first X-ray limiter 13 are received. In an identical manner, the operations with respect to the second X-ray limiter 17 too can be received. For example, the operator can operate the arm switching button 2324b, which is illustrated in FIG. 13, in order to switch the operation target; and can perform operations with respect to the second X-ray limiter 17 in an identical manner to the first X-ray limiter 13.

In the embodiments described above, the X-ray diagnosis apparatus is a biplane apparatus. However, the embodiments are not limited to that case. Alternatively, for example, the X-ray diagnosis apparatus 1 can be a single plane device. As an example, the X-ray diagnosis apparatus 1 can be configured not to include the second X-ray tube 16, the second X-ray limiter 17, the second X-ray detector 18, and the second arm 19.

When the X-ray diagnosis apparatus 1 is a single plane device, the diaphragm operation console 232 can be configured not to include the switches for switching between receiving operations with respect to the first X-ray limiter 13 and receiving operations with respect to the second X-ray limiter 17. For example, the diaphragm operation console 232 can be configured not to include the arm switching buttons 2324a and 2324b illustrated in FIG. 13. That enables achieving further downsizing of the diaphragm operation console 232, or enables increasing the size of the operating units other than the arm switching buttons 2324a and 2324b.

In the embodiments described above, the diaphragm operation console 232 is installed on the bed. However, the embodiments are not limited to that case. For example, the X-ray diagnosis apparatus 1 can be configured to further include a stand on casters, and the diaphragm operation console 232 can be installed on the stand. Apart from that, the diaphragm operation console 232 can be installed in an arbitrary component of the X-ray diagnosis apparatus 1, such as on the first arm 15 or the second arm 19.

Figure 17:
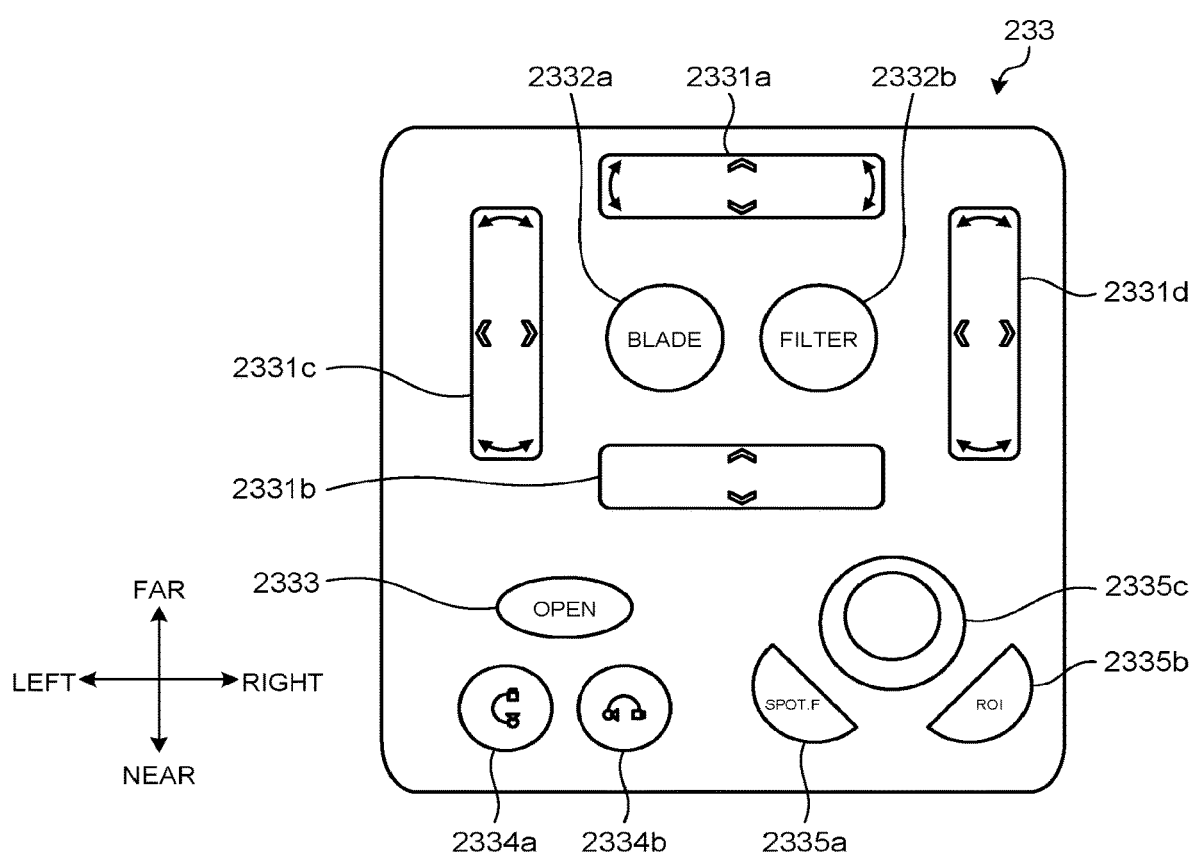
FIGS. 17 and 18 are diagrams illustrating an example of a console according to a third embodiment.
Figure 18:
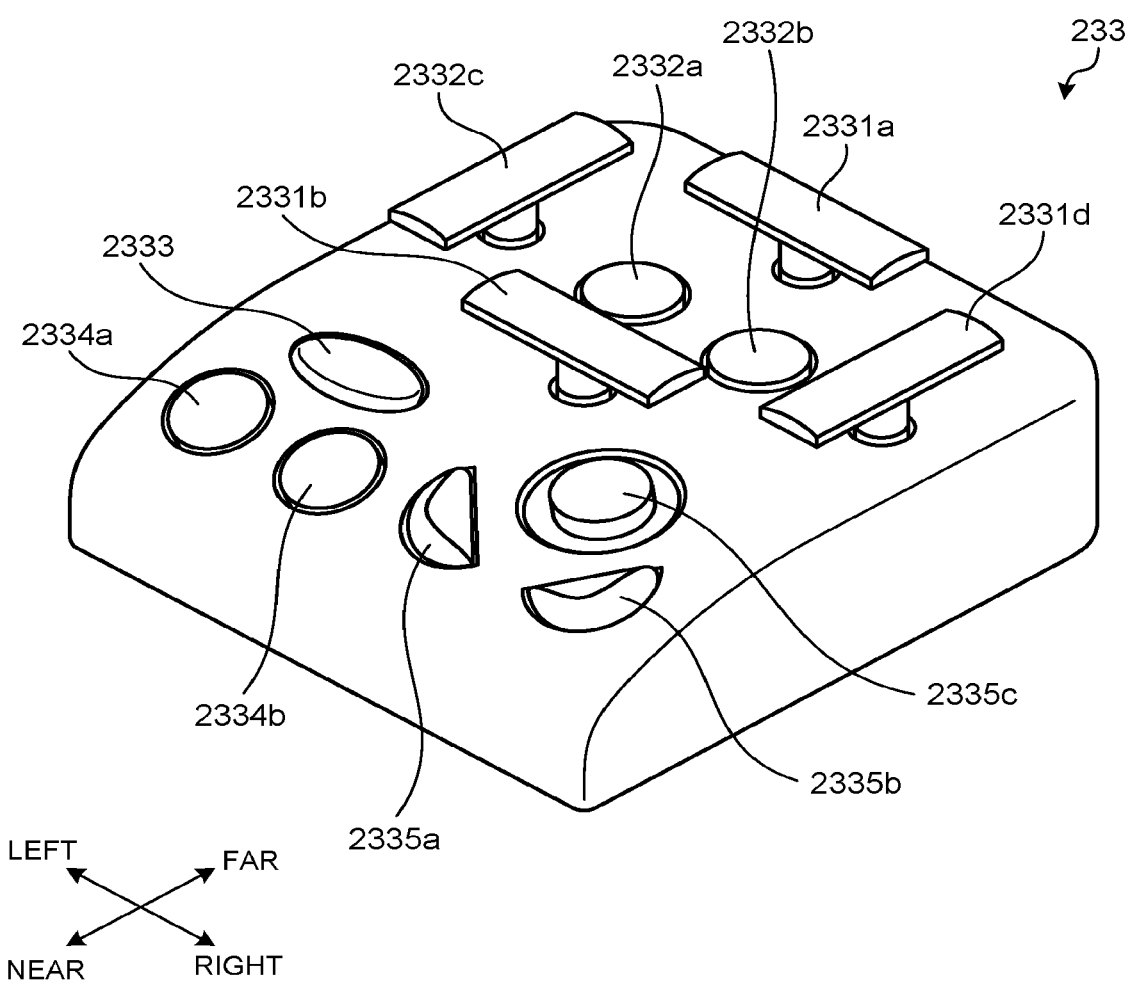

In the embodiments described above, as an example of the arrangement of the operating units, only the arrangement illustrated in FIG. 13 is explained as an example. However, the embodiments are not limited to that arrangement. That is, the arrangement of the operating units on the diaphragm operation console 232 illustrated in FIG. 13 is only exemplary, and can be appropriately changed. For example, the operating units can be arranged as illustrated on a diaphragm operation console 233 illustrated in FIGS. 17 and 18. FIGS. 17 and 18 are diagrams illustrating an example of a console according to a third embodiment.

As illustrated in FIGS. 17 and 18, the diaphragm operation console 233 has the following components arranged therein: sticks 2331a, 2331b, 2331c, and 2331d; switching buttons 2332a and 2332b; an open button 2333; arm switching buttons 2334a and 2334b; fluoroscopy mode switching buttons 2335a and 2335b; and an operation stick 2335c.

The arm switching buttons 2334a and 2334b correspond to the arm switching buttons 2324a and 2324b, respectively, illustrated in FIG. 13. That is, the arm switching buttons 2324a and 2324b are switches for switching between receiving operations with respect to the first X-ray limiter 13 and receiving operations with respect to the second X-ray limiter 17. For example, when the arm switching button 2334a is selected, according to the input operation received via the diaphragm operation console 233, the acquisition function 241 controls the operations of the first X-ray limiter 13 held by the first arm 15. On the other hand, when the arm switching button 2334b is selected, according to the input operation received via the diaphragm operation console 233, the acquisition function controls the operations of the second X-ray limiter 17 held by the second arm 19. The following explanation is given for the case in which the arm switching button 2334a is selected, and the operations with respect to the first X-ray limiter 13 are received.

The sticks 2331a, 2331b, 2331c, and 2331d are operating units corresponding to the sticks 2321a, 2321b, 2321c, and 2321d, respectively, illustrated in FIG. 13. For example, when the diaphragm mode is set, the far-side stick 2331a receives operations with respect to the upper diaphragm blade 131a; the near-side stick 2331b receives operations with respect to the lower diaphragm blade 131b; the left-side stick 2331c receives operations with respect to the left-side diaphragm blade 131c; and the right-side stick 2331d receives operations with respect to the right-side diaphragm blade 131d.

The switching buttons 2332a and 2332b correspond to the switching buttons 2322a and 2322b, respectively, illustrated in FIG. 13. That is, the switching buttons 2332a and 2332b are switching units for switching between the diaphragm mode that is meant for operating the diaphragm blades and the filter mode that is meant for operating the compensating filters. For example, when the switching button 2332a indicated by "BLADE" is selected, according to the input operation received via the diaphragm operation console 233, the acquisition function 241 controls the operations of the diaphragm blades 131a, 131b, 131c, and 131d. Alternatively, when the switching button 2332b indicated by "FILTER" is selected, according to the input operation received via the diaphragm operation console 233, the acquisition function 241 controls the operations of the compensating filters 132a, 132b, and 132c.

The open button 2333 corresponds to the open button 2323 illustrated in FIG. 13. That is, the open button 2333 is a button for causing retraction of the four diaphragm blades all at once. For example, when the open button 2333 is operated by the operator; the acquisition function 241 causes retraction of the diaphragm blades 131a, 131b, 131c, and 131d all at once to an external area excluded from the X-ray irradiation area. Meanwhile, the configuration can be such that, when the open button 2333 is operated, the acquisition function 241 causes retraction of the four diaphragm blades as well as the compensating filters.

The fluoroscopy mode switching buttons 2335a and 2335b correspond to the fluoroscopy mode switching buttons 2325a and 2325b, respectively, illustrated in FIG. 13. That is, the fluoroscopy mode switching buttons 2335a and 2335b are switches for switching between the fluoroscopy modes. For example, when the fluoroscopy mode switching button 2335a indicated by "SPOT.F" is selected, the acquisition function 241 sets the spot fluoroscopy mode as the fluoroscopy mode. On the other hand, when the fluoroscopy mode switching button 2335b indicated by "ROI" is selected, the acquisition function 241 sets the spot ROI mode as the fluoroscopy mode.

The operation stick 2335c corresponds to the operation stick 2325c illustrated in FIG. 13. That is, when the spot fluoroscopy mode is set, the operation stick 2335c moves the X-ray irradiation area, which is formed by the four diaphragm blades, with respect to the subject P while maintaining the shape of the X-ray irradiation area. When the spot ROI mode is set, the operation stick 2335c moves, with respect to the subject P, the area in which X-rays are bombarded onto the subject P without any attenuation attributed to the radiation dose reduction filter.

In an identical manner to the case of the diaphragm operation console 232, the hardware meant for implementing the operating units of the diaphragm operation console 233 can be appropriately changed. For example, with reference to FIGS. 17 and 18, four sticks (the sticks 2331a, 2331b, 2331c, and 2331d) are illustrated that receive inclination operations. However, instead of including the four sticks, the diaphragm operation console 233 can include some other hardware such as four operating units that receive sliding operations or four wheel-shaped operating units. In an identical manner, the switching buttons 2332a and 2332b, the open button 2333, the arm switching buttons 2334a and 2334b, the fluoroscopy mode switching buttons 2335a and 2335b, and the operation stick 2335c can be implemented using some other hardware.

Moreover, in an identical manner to the case of the diaphragm operation console 232, some operating units of the diaphragm operation console 233 can be appropriately omitted. For example, when the first X-ray limiter 13 and the second X-ray limiter 17 respectively include three diaphragm blades, the diaphragm operation console 233 can include only three operating units, from among the four operating units (the sticks 2331a, 2331b, 2331c, and 2331d) illustrated in FIGS. 17 and 18, corresponding to the three diaphragm blades. Alternatively, for example, when neither the first X-ray limiter 13 nor the second X-ray limiter 17 includes any diaphragm blade or when neither the first X-ray limiter 13 nor the second X-ray limiter 17 includes any compensating filter, the diaphragm operation console 233 can be configured not to include the switching buttons 2332a and 2332b. Meanwhile, for example, when the X-ray diagnosis apparatus 1 is a single plane device, the diaphragm operation console 233 can be configured not to include the arm switching buttons 2334a and 2334b.

The constituent elements of the devices illustrated in the drawings are merely conceptual, and need not be physically configured as illustrated. The constituent elements, as a whole or in part, can be separated or integrated either functionally or physically based on various types of loads or use conditions. The process functions of the device are entirely or partially implemented by the CPU or computer programs that are analyzed and executed by the CPU, or implemented as hardware by wired logic.

The control methods explained in the embodiments described above can be implemented as a result of executing a control program, which is written in advance, in a computer such as a personal computer or a workstation. The control program can be distributed via a network such as the Internet. Alternatively, the medical information processing program can be recorded in a computer-readable non-transitory recording medium such as a hard disk, a flexible disk (FD), a compact disk read only memory (CD-ROM), a magneto optical (MO) disk, or a digital versatile disk (DVD), and the computer can read the control program from the recording medium and execute it.

According to at least one aspect described above, it becomes possible to enhance the operability related to at least either the diaphragm blades or the compensating filters.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnosis apparatus, comprising:
an X-ray limiter including four diaphragm blades; and
a console on which four physical operating units are placed at four positions, the four physical operating units corresponding to the four diaphragm blades, wherein
when viewed from a side of an operator of the console, the four physical operating units are placed on a far side, a near side, a left side, and a right side,
the four physical operating units include a far-side operating unit, a near-side operating unit, a left-side operating unit, and a right-side operating unit and correspond to an upper diaphragm blade, a lower diaphragm blade, a left-side diaphragm blade, and a right-side diaphragm blade, respectively, with reference to an X-ray image displayed on a display,
an operation of moving the far-side operating unit in a far-side direction results in movement of the upper diaphragm blade in an upward direction of the X-ray image displayed on the display, and an operation of moving the far-side operating unit in a near-side direction results in movement of the upper diaphragm blade in a downward direction of the X-ray image displayed on the display,
an operation of moving the near-side operating unit in the far-side direction results in movement of the lower diaphragm blade in the upward direction of the X-ray image displayed on the display, and an operation of moving the near-side operating unit in the near-side direction results in movement of the lower diaphragm blade in the downward direction of the X-ray image displayed on the display,
an operation of moving the left-side operating unit in a leftward direction results in movement of the left-side diaphragm blade in a leftward direction of the X-ray image displayed on the display, and an operation of moving the left-side operating unit in a rightward direction results in movement of the left-side diaphragm blade in a rightward direction of the X-ray image displayed on the display, and
an operation of moving the right-side operating unit in the leftward direction results in movement of the right-side diaphragm blade in the leftward direction of the X-ray image displayed on the display, and an operation of moving the right-side operating unit in the rightward direction results in movement of the right-side diaphragm blade in the rightward direction of the X-ray image displayed on the display.

2. The X-ray diagnosis apparatus according to claim 1, wherein
the X-ray limiter further includes at least one compensating filter,
the console further includes a switch to switch between a diaphragm mode, which is set for operating the four diaphragm blades, and a filter mode, which is set for operating the at least one compensating filter,
when the diaphragm mode is set, the four operating units receive an operation with respect to the four diaphragm blades, and when the filter mode is set, at least one of the four operating units receive an operation with respect to the at least one compensating filter.

3. The X-ray diagnosis apparatus according to claim 2, wherein
the X-ray limiter includes
a first compensating filter that is inserted from a left side with respect to the X-ray image displayed on the display, and
a second compensating filter that is inserted from a right side with respect to the X-ray image displayed on the display, and
the left-side operating unit and the right-side operating unit receive an operation with respect to the first compensating filter and the second compensating filter, respectively.

4. The X-ray diagnosis apparatus according to claim 3, wherein
the left-side operating unit and the right-side operating unit are rotatable in a clockwise direction and a counterclockwise direction,
when the filter mode is set,
the operation of moving the left-side operating unit in the leftward direction results in movement of the first compensating filter in the leftward direction of the X-ray image displayed on the display,
the operation of moving the left-side operating unit in the rightward direction results in movement of the first compensating filter in the rightward direction of the X-ray image displayed on the display,
an operation of rotating the left-side operating unit in the clockwise direction results in rotation of the first compensating filter in a clockwise direction of the X-ray image displayed on the display, and
an operation of rotating the left-side operating unit in the counterclockwise direction results in rotation of the first compensating filter in a counterclockwise direction of the X-ray image displayed on the display, and
when the filter mode is set,
the operation of moving the right-side operating unit in the leftward direction results in movement of the second compensating filter in the leftward direction of the X-ray image displayed on the display,
the operation of moving the right-side operating unit in the rightward direction results in movement of the second compensating filter in the rightward direction of the X-ray image displayed on the display,
an operation of rotating the right-side operating unit in the clockwise direction results in rotation of the second compensating filter in the clockwise direction with respect to the X-ray image displayed on the display, and
an operation of rotating the right-side operating unit in the counterclockwise direction results in rotation of the second compensating filter in the counterclockwise direction with respect to the X-ray image displayed on the display.

5. The X-ray diagnosis apparatus according to claim 3, wherein
the X-ray limiter further includes a third compensating filter that is inserted from an upper side with respect to the X-ray image displayed on the display, and
the far-side operating unit receives an operation with respect to the third compensating filter.

6. The X-ray diagnosis apparatus according to claim 5, wherein
the far-side operating unit is rotatable in a clockwise direction and a counterclockwise direction, and
when the filter mode is set,
the operation of moving the far-side operating unit in the far-side direction results in movement of the third compensating filter in the upward direction of the X-ray image displayed on the display,
the operation of moving the far-side operating unit in the near-side direction results in movement of the third compensating filter in the downward direction of the X-ray image displayed on the display,
an operation of rotating the far-side operating unit in the clockwise direction results in rotation of the third compensating filter in a clockwise direction with respect to the X-ray image displayed on the display, and
an operation of rotating the far-side operating unit in the counterclockwise direction results in rotation of the third compensating filter in a counterclockwise direction with respect to the X-ray image displayed on the display.

7. The X-ray diagnosis apparatus according to claim 3, wherein
the left-side operating unit and the right-side operating unit are movable in the far-side direction and the near-side direction,
when the filter mode is set,
the operation of moving the left-side operating unit in the leftward direction results in movement of the first compensating filter in the leftward direction of the X-ray image displayed on the display,
the operation of moving the left-side operating unit in the rightward direction results in movement of the first compensating filter in the rightward direction of the X-ray image displayed on the display,
an operation of moving the left-side operating unit in the far-side direction results in rotation of the first compensating filter in a clockwise direction with respect to the X-ray image displayed on the display, and
an operation of moving the left-side operating unit in the near-side direction results in rotation of the first compensating filter in a counterclockwise direction with respect to the X-ray image displayed on the display, and
when the filter mode is set,
the operation of moving the right-side operating unit in the leftward direction results in movement of the second compensating filter in the leftward direction of the X-ray image displayed on the display,
the operation of moving the right-side operating unit in the rightward direction results in movement of the second compensating filter in the rightward direction of the X-ray image displayed on the display,
an operation of moving the right-side operating unit in the near-side direction results in rotation of the second compensating filter in the clockwise direction with respect to the X-ray image displayed on the display, and
an operation of moving the right-side operating unit in the far-side direction results in rotation of the second compensating filter in the counterclockwise direction with respect to the X-ray image displayed on the display.

8. The X-ray diagnosis apparatus according to claim 7, wherein
the X-ray limiter further includes a third compensating filter, and
the far-side operating unit receives an operation with respect to the third compensating filter.

9. The X-ray diagnosis apparatus according to claim 8, wherein
the far-side operating unit is movable in the rightward direction and the leftward direction, and
when the filter mode is set,
the operation of moving the far-side operating unit in the far-side direction results in movement of the third compensating filter in the upward direction of the X-ray image displayed on the display,
the operation of moving the far-side operating unit in the near-side direction results in movement of the third compensating filter in the downward direction of the X-ray image displayed on the display,
an operation of moving the far-side operating unit in the rightward direction results in rotation of the third compensating filter in the clockwise direction with respect to the X-ray image displayed on the display, and
an operation of moving the far-side operating unit in the leftward direction results in rotation of the third compensating filter in the counterclockwise direction with respect to the X-ray image displayed on the display.

10. The X-ray diagnosis apparatus according to claim 2, wherein, among the four physical operating units, an operating unit corresponding to a compensating filter is different from an operating unit not corresponding to the compensating filter.

11. The X-ray diagnosis apparatus according to claim 10, wherein, among the four physical operating units, the operating unit corresponding to the compensating filter has a different shape than the operating unit not corresponding to the compensating filter.

12. The X-ray diagnosis apparatus according to claim 1, wherein
the four physical operating units are formed using sticks that receive an inclination operation,
an operation of inclining the far-side operating unit in far-side direction results in the movement of the upper diaphragm blade in the upward direction of the X-ray image displayed on the display, and an operation of inclining the far-side operating unit in the near-side direction results in the movement of the upper diaphragm blade in the downward direction of the X-ray image displayed on the display,
an operation of inclining the near-side operating unit in the far-side direction results in the movement of the lower diaphragm blade in the upward direction of the X-ray image displayed on the display, and an operation of inclining the near-side operating unit in the near-side direction results in the movement of the lower diaphragm blade in the downward direction of the X-ray image displayed on the display,
an operation of inclining the left-side operating unit in the leftward direction results in the movement of the left-side diaphragm blade in the leftward direction of the X-ray image displayed on the display, and an operation of inclining the left-side operating unit in the rightward direction results in the movement of the left-side diaphragm blade in the rightward direction of the X-ray image displayed on the display, and
an operation of inclining the right-side operating unit in the leftward direction results in the movement of the right-side diaphragm blade in the leftward direction of the X-ray image displayed on the display, and an operation of inclining the right-side operating unit in the rightward direction results in the movement of the right-side diaphragm blade in the rightward direction of the X-ray image displayed on the display.

13. The X-ray diagnosis apparatus according to claim 1, wherein the console further includes a button, located at a position enclosed by the four physical operating units, to cause retraction of the four diaphragm blades all at once.

14. The X-ray diagnosis apparatus according to claim 1, wherein the console further includes a particular operating unit that moves a position of an X-ray irradiation area, which is formed by the four diaphragm blades, with respect to a subject, while maintaining a shape of the X-ray irradiation area.

15. The X-ray diagnosis apparatus according to claim 1, wherein
the console further includes a coordination setting switch that switches to a coordinated-movement mode, and
when the coordinated-movement mode is set,
the upper diaphragm blade and the lower diaphragm blade perform coordinated movement, and
the left-side diaphragm blade and the right-side diaphragm blade perform coordinated movement.

16. The X-ray diagnosis apparatus according to claim 15, wherein
in the coordinated-movement mode, when either the far-side operating unit or the near-side operating unit is operated, the upper diaphragm blade and the lower diaphragm blade move in a symmetrical manner, and
in the coordinated-movement mode, when either the left-side operating unit or the right-side operating unit is operated, the left-side diaphragm blade and the right-side diaphragm blade move in a symmetrical manner.

17. The X-ray diagnosis apparatus according to claim 1, wherein
the X-ray diagnosis apparatus is a biplane apparatus having a first arm and a second arm,
the first arm holds the X-ray limiter, which is a first X-ray limiter,
the X-ray diagnosis apparatus further includes a second X-ray limiter held by the second arm, and
the console further includes a switch to switch between a receiving operation with respect to the first X-ray limiter held by the first arm and a receiving operation with respect to the second X-ray limiter held by the second arm.

18. The X-ray diagnosis apparatus according to claim 1, wherein the console further includes a switch to switch between
a first fluoroscopy mode,
which is a fluoroscopy mode to display a first area, in which X-rays are bombarded onto a subject without getting blocked by the four diaphragm blades as well as without getting attenuated due to a radiation dose reduction filter, and a second area which represents a surrounding area of the first area, and
which is to display, as the second area, X-ray images acquired previously, and
a second fluoroscopy mode to display, as the second area, X-ray images that are sequentially acquired using X-rays that have transmitted through the radiation dose reduction filter.

19. A console on which four physical operating units are placed at four positions, the four physical operating units corresponding to four diaphragm blades of an X-ray diagnosis apparatus, wherein when viewed from a side of an operator of the console, the four physical operating units are placed on a far side, a near side, a left side, and a right side, the four physical operating units include a far-side operating unit, a near-side operating unit, a left-side operating unit, and a right-side operating unit and correspond to an upper diaphragm blade, a lower diaphragm blade, a left-side diaphragm blade, and a right-side diaphragm blade, respectively, with reference to an X-ray image displayed on a display, an operation of moving the far-side operating unit in a far-side direction results in movement of the upper diaphragm blade in an upward direction of the X-ray image displayed on the display, and an operation of moving the far-side operating unit in a near-side direction results in movement of the upper diaphragm blade in a downward direction of the X-ray image displayed on the display, an operation of moving the near-side operating unit in the far-side direction results in movement of the lower diaphragm blade in the upward direction of the X-ray image displayed on the display, and an operation of moving the near-side operating unit in the near-side direction results in movement of the lower diaphragm blade in the downward direction of the X-ray image displayed on the display, an operation of moving the left-side operating unit in a leftward direction results in movement of the left-side diaphragm blade in a leftward direction of the X-ray image displayed on the display, and an operation of moving the left-side operating unit in a rightward direction results in movement of the left-side diaphragm blade in a rightward direction of the X-ray image displayed on the display, and an operation of moving the right-side operating unit in the leftward direction results in movement of the right-side diaphragm blade in the leftward direction of the X-ray image displayed on the display, and an operation of moving the right-side operating unit in the rightward direction results in movement of the right-side diaphragm blade in the rightward direction of the X-ray image displayed on the display.

20. An X-ray diagnosis apparatus, comprising:

an X-ray limiter that includes four diaphragm blades;

a bed that has a tabletop on which a subject is placed; and a console installed laterally on the bed and on which four physical operating units are placed at four positions, the four physical operating units corresponding to the four diaphragm blades, wherein of two sides of the bed, when viewed from a side on which the console is installed, the four physical operating units are placed on a far side, a near side, a left side, and a right side, and the four physical operating units include a far-side operating unit, a near-side operating unit, a left-side operating unit, and a right-side operating unit and receive an operation for moving an upper diaphragm blade, a lower diaphragm blade, a left-side diaphragm blade, and a right-side diaphragm blade, respectively, with reference to an X-ray image displayed on a display.

* * * * *